(12) United States Patent
Nagasaki et al.

(10) Patent No.: US 8,980,241 B2
(45) Date of Patent: Mar. 17, 2015

(54) POLYMERIZED CYCLIC NITROXIDE RADICAL COMPOUND AND USE THEREOF

(75) Inventors: Yukio Nagasaki, Tsukuba (JP); Toru Yoshitomi, Tsukuba (JP); Hirofumi Matsui, Tsukuba (JP); Aki Hirayama, Tsuchiura (JP); Takashi Mamiya, Tsukuba (JP); Akira Matsumura, Tsukuba (JP); Kensuke Suzuki, Tsukuba (JP); Hideo Tsurushima, Tsukuba (JP); Aiki Marushima, Tsukuba (JP); Kazuko Toh, Tsukuba (JP); Daisuke Miyamoto, Nobeoka (JP)

(73) Assignee: University of Tsukuba, Ibaraki (JP)

( * ) Notice: Subject to any disclaimer, the term of this patent is extended or adjusted under 35 U.S.C. 154(b) by 888 days.

(21) Appl. No.: 12/990,575

(22) PCT Filed: Dec. 4, 2008

(86) PCT No.: PCT/JP2008/072467
§ 371 (c)(1),
(2), (4) Date: Feb. 28, 2011

(87) PCT Pub. No.: WO2009/133647
PCT Pub. Date: Nov. 5, 2009

(65) Prior Publication Data
US 2011/0142787 A1    Jun. 16, 2011

(30) Foreign Application Priority Data

May 2, 2008 (JP) ................................ 2008-120626
Jul. 8, 2008 (JP) ................................ 2008-178150

(51) Int. Cl.
| | | |
|---|---|---|
| A61K 31/74 | (2006.01) |
| C08F 8/30 | (2006.01) |
| A23L 1/30 | (2006.01) |
| A61K 47/48 | (2006.01) |
| A61K 49/08 | (2006.01) |
| A61K 49/12 | (2006.01) |
| A61K 49/18 | (2006.01) |
| A61K 49/20 | (2006.01) |
| B82Y 5/00 | (2011.01) |
| C08G 65/333 | (2006.01) |
| C08G 65/334 | (2006.01) |
| C08G 73/10 | (2006.01) |
| C08L 71/02 | (2006.01) |
| C08L 23/00 | (2006.01) |
| C08L 25/00 | (2006.01) |
| C08L 71/03 | (2006.01) |
| C08L 79/00 | (2006.01) |

(52) U.S. Cl.
CPC ... *C08F 8/30* (2013.01); *A23L 1/30* (2013.01); *A61K 47/48176* (2013.01); *A61K 47/48215* (2013.01); *A61K 49/085* (2013.01); *A61K 49/126* (2013.01); *A61K 49/1806* (2013.01); *A61K 49/1824* (2013.01); *A61K 49/20* (2013.01); *B82Y 5/00* (2013.01); *C08G 65/33396* (2013.01); *C08G 65/334* (2013.01); *C08G 65/3344* (2013.01); *C08G 73/1071* (2013.01); *C08G 2261/126* (2013.01); *C08L 23/00* (2013.01); *C08L 25/00* (2013.01); *C08L 71/02* (2013.01); *C08L 71/03* (2013.01); *C08L 79/00* (2013.01); *C08L 2203/02* (2013.01); *C08L 2205/05* (2013.01)
USPC ........................... 424/78.17; 435/28; 525/539

(58) Field of Classification Search
CPC combination set(s) only.
See application file for complete search history.

(56) References Cited

U.S. PATENT DOCUMENTS

| | | | |
|---|---|---|---|
| 5,925,720 | A | 7/1999 | Kataoka et al. |
| 5,929,177 | A | 7/1999 | Kataoka et al. |
| 2003/0129151 | A1 | 7/2003 | Candau et al. |
| 2005/0058612 | A1 | 3/2005 | Candau et al. |

FOREIGN PATENT DOCUMENTS

| | | |
|---|---|---|
| JP | 5-117385 | 5/1993 |
| JP | 6-206815 | 7/1994 |
| JP | 2002-170568 | 6/2002 |
| JP | 2003-137719 | 5/2003 |
| JP | 2005-29480 | 2/2005 |
| JP | 2006-321763 | 11/2006 |
| WO | 96/32967 | 10/1996 |
| WO | 2006/084198 | 8/2006 |

OTHER PUBLICATIONS

International Search Report issued Mar. 17, 2009 in corresponding International (PCT) Application No. PCT/JP2008/072467, of record.
International Preliminary Report on Patentability with English translation of the Written Opinion issued Dec. 23, 2010 in corresponding International (PCT) Application No. PCT/JP2008/072467.
Soule et al., "The chemistry and biology of nitroxide compounds", Free Radical Biology and Medicine, vol. 42, pp. 1632-1650 (2007).

(Continued)

*Primary Examiner* — Hasan Ahmed
(74) *Attorney, Agent, or Firm* — Wenderoth, Lind & Ponack, L.L.P.

(57) ABSTRACT

A method of covalently bonding a cyclic nitroxide radical compound to a hydrophobic block of a specific hydrophylic-phobic block copolymer, and polymerized cyclic nitroxide radical compound copolymerized in this manner, as well as use of such a compound, for instance, in the medical field are provided. The compound demonstrates long term stability in vivo under reductive environment.

4 Claims, 10 Drawing Sheets

(56) References Cited

OTHER PUBLICATIONS

Kawm et al., "Effects of a Novel Free Radical Scavenger, MCI-186, on Ischemic Brain Damage in the Rat Distal Middle Cerebral Artery Occlusion Model", The Journal of Pharmacology and Experimental Therapeutics, vol. 281, No. 2, pp. 921-927 (1997).

Toru Yoshitomi, "Synthesis of acetal-poly(ethylene glycol)-*b*-poly(chloromethylstyrene) and application", Abstract used in class, Graduate School of Pure and Applied Sciences, University of Tsukuba (Sep. 27, 2007), with English translation.

The 18$^{th}$ Symposium of The Materials Research Society of Japan, Program and Abstracts, with partial English translation, Dec. 7, 2007, with partial English translation.

Yoshitomo et al., "Synthesis of acetal-poly(ethylene glycol)-*b*-poly(chloromethylstyrene) and application for functional bioimaging nanosphere", The Materials Research Society of Japan, Dec. 8, 2007, with partial English translation.

(NUMBER OF TIMES REPRECIPITATED: 0, ■ ; 1, ● ; 2, ▲ ; 3, ▽)

Femoral vein Injection (i.v.)   Carotid artery Injection (i.v.)

** P<0.01
*P<0.05

*P<0.05

POLYMERIZED CYCLIC NITROXIDE RADICAL COMPOUND AND USE THEREOF

TECHNICAL FIELD

The invention relates to a method for stabilizing cyclic nitroxide radical compound, as well as a polymerized cyclic nitroxide radical compound and use thereof.

BACKGROUND ART

In recent years, electron spin resonance (ESR) imaging by way of reactive oxygen species and radical species for tracing reactions in vitro and the use of stable radicals in the prevention, treatment or the like, of diseases or symptoms in which the reactive oxygen species are involved, have been drawing attention.

The ESR method has been used widely under in and ex vivo environments, using signal analysis and the spin trapping method, for L band ESR imaging, generation and annihilation of reactive oxygen species, and the like. Although the ESR-active electronic spin is known to be an extremely unstable reactive species, for stable cyclic nitroxide radicals such as the 2,2,6,6-tetramethylpiperidino oxy radical (TEMPO), the radical being stabilized, even more various applications are being developed, and in addition, examined (for instance, refer to Non-patent Reference 1 mentioned below). However, the current situation is that such stable cyclic nitroxide radicals are difficult to handle, as the radical or even the stable electronic spin is reduced in a short time in the presence of a reducing species such as ascorbic acid, which is present in vivo.

Note that one of the uses mentioned above, the so-called spin labeling method, is a method whereby stable nitroxide radicals are used as labeling agents for conjugation to proteins, fatty acids or steroids; however this is not intended to stabilize further the stable nitroxide radicals under an external environment, and no improved stabilization can be expected either. In addition, covalently bonding a plurality of stable nitroxide radicals, along with one or a plurality of metal ions/chelaters, to a polymer or an oligomer to try an add a novel function to an MRI contrast medium has also been proposed (for instance, refer to Patent Reference 1 mentioned below).

Meanwhile, it is also known that reactive oxygen species and reactive radical species play important roles in vivo. For instance, a free radical such as the hydroxy radical has been cited as one of the causes involved in the damage of a brain. Typically, it is known that free radicals tend to appear in the penumbra (ischemic penumbra) region, considered as the drug treatment region, during cerebral ischemia or after reperfusion. Therefore, some free radical scavengers have drawn attention as brain protecting agents that eliminate/render harmless a radical causing damages to brain vessels and neuronal cells, and as one among such scavengers, Edaravone (3-methyl-1-phenyl-2-pyrazolin-5-one) is sold commercially under the product name Radicut (refer to Non-patent Reference 2 mentioned below). However, it is also known that the use of Edaravone is accompanied by a risk of the adverse effect of acute kidney failure (kidney function disorder, liver function disorder and heart disease as complications). In addition, it is thought that there is room for improvement from the aspect of the effect and the aspect of safety, since in human, from the aspect of safety, Edaravone is administered multiple times by dividing into smaller amounts than the dose for which remarkable effects are observed in animal experiments.

In addition, it has been discovered that the cyclic nitroxide compounds classified in the above stable cyclic nitroxide radicals, 4-hydroxy-2,2,6,6-tetramethylpiperidine-1-oxyl (Tempol) to begin with, which has unique antioxidant properties, have the ability to decompose a superoxide or a peroxide, thereby functioning as radical scavengers, altering oxidative stress and altering the redox state of a tissue, and thereby interacting with and then altering many metabolic processes (refer to Non-patent Reference 3 mentioned below). Then, in Non-patent Reference 3, it has been suggested that these interactions could be used in therapeutic and research applications including protection against ionizing radiations, probes for functional magnetic resonance imaging, prevention or treatment of cancer, regulation of hypertension and body weight, and defense against damages caused by ischemia and reperfusion. However, once they have entered inside an organism, cyclic nitroxide compounds no longer function as radical scavengers if they are reduced by an endogenous reducing agent such as ascorbic acid.

In prior art, the present inventors have shown that nanoparticles (or polymeric micelles) from the self-assemblage of hydrophylic-phobic type block copolymers in water function as novel materials enabling drug carriers and nano-diagnoses, and have moved various material designs forward. In particular, by introducing a functional group at the water-soluble macromolecular end of the hydrophylic-phobic block copolymer, core-shell type nanoparticles with tens of nanometers in size having a ligand insertion site on the surface layer hold expectations as novel drug carriers enabling active targeting (for instance, refer to Patent Reference 2 and Patent Reference 3 mentioned below).

Patent Reference 1: Japanese Translation of PCT Application No. 2001-523215 (or WO96/32967)
Patent Reference 2: WO96/33233 (or U.S. Pat. No. 5,925, 720)
Patent Reference 3: WO97/06202 (or U.S. Pat. No. 5,929, 177)
Non-patent Reference 1: B. P. Soule et al., Free Radical Biology & Medicine 42 (2007) 1632-1650
Non-patent Reference 2: J. Pharmacol. Exp. Ther. 281: 921- 927, 1997
Non-patent Reference 3: James B. Mitchell, et al., Free Radical Biology & Medicine 42 (2007) 1632-650

DISCLOSURE OF THE INVENTION

As described above, stable cyclic nitroxide radicals such as Tempol, while referred to as "stable", function as radical scavengers; however, under biological reducing environment they become reduced and no longer function as radical scavengers. Concretely, medical uses of the cyclic nitroxide radicals alone as contrast media or therapeutic agents were difficult, since, in vivo, they are reduced in a short time or readily in the presence of reducing species such as, for instance, ascorbic acid. Therefore, it would be meaningful if the provision of means allowing radical species to be introduced and maintained in vivo stably over a long time were possible.

The present inventors introduced this time stable nitroxide radicals (TEMPO or the like) into the hydrophobic segments of specific block copolymers, performed preparations of novel nanoparticles (RNPs) having stable nitroxide radicals mainly in the core regions, examined the disposition thereof, and verified that a significantly high stability in blood in contrast to stable nitroxide radicals could be conferred. (The 18th Symposium of The Materials Society of Japan, Program and Abstracts, 7 Dec. 2007; Issued by: The 18th MRS-J Academic Symposium Organization Committee; Issued from: The Secretariat of MRS-J).

In addition, they found that such polymeric micellized cyclic nitroxide radical compounds could prevent or treat damages to brain cells, which are presumed to be caused by free radicals produced in ischemic areas and the like. This being the case, it is presumed that the polymeric micellized cyclic nitroxide radical compounds can translocate within the brain without being affected to translocation limitation within the brain by the blood-brain barrier, and furthermore, exerted within the brain their original actions as radical scavengers. In addition, it was also verified that the compounds, when administered into an artery or a vein at doses enabling the prevention or the treatment of brain cell damages, do not demonstrate marked toxicity or serious adverse effects against test animals. Taking into consideration that the brain damage prevention or treatment describe above is presumed to be due to the free radical scavenging action of the polymeric micellized cyclic nitroxide radical compounds, regardless of which mode of production mechanism of reactive oxygen species or free radicals (or hydroxy radicals) inside the brain may be, in an organism in which reactive oxygen species or free radicals were generated, the compounds are thought to be able to prevent or treat a wide range of diseases or symptoms in which reactive oxygen species or free radicals are involved.

Consequently, the present application discloses an invention with the following modes.

First Mode:

A stabilization method for a cyclic nitroxide radical compound, the method comprising a step of covalently bonding a cyclic nitroxide radical compound to a block copolymer containing a poly(ethylene glycol) chain segment and a hydrophobic chain segment carrying a reactive group through a functional group other than the radical of the compound and the reactive group of the copolymer, the functional group being an amino group, an aminomethyl group, a hydroxy group, a hydroxymethyl group, a carboxyl group or a carboxymethyl group, the reactive group being a halogen atom, a carboxyl group, an isocyanate residue, an isothiocyanate residue, an ester residue, an acid anhydride residue, a boronic acid residue, a maleimide residue or an epoxy group, and the block copolymer being able to form a polymeric micelle in an aqueous solvent in a form in which the cyclic nitroxide radical compound is covalently bonded.

Second Mode:

A polymerized nitroxide radical compound obtainable by such a stabilization method.

The polymerized nitroxide radical compound comprising poly(ethylene glycol) chain segments in which the repeating unit of ethylene oxide is 15 to 10,000 and a polystyrene chain segments in which the repeating unit of styrene is 3 to 3,000, and, at least 10%, preferably 30%, more preferably 50%, even more preferably 80% and particularly preferably 100% of the repeating units of styrene in the polystyrene chain segment, at position 4 of the phenyl group, a residue of cyclic nitroxide radical compound being covalently bonded through a linking group selected from the group consisting of —CH$_2$NH—, —CH$_2$NHCH$_2$—, —CH$_2$O—, —CH$_2$OCH$_2$—, —CH$_2$OCO— and —CH$_2$OCOCH$_2$—, when present, the remainder of the position 4 being a halogen atom, a hydrogen atom or a hydroxyl group and the residue of cyclic nitroxide radical compound being selected from the group consisting of 2,2,6,6-tetramethylpiperidine-1-oxyl-4-yl, 2,2,5,5-tetramethylpyrrolidine-1-oxyl-3-yl, 2,2,5,5-tetramethylpyrroline-1-oxyl-3-yl and 2,4,4-trimethyl-1,3-oxazolidine-3-oxyl-2-yl, 2,4,4-trimethyl-1,3-thiazolidine-3-oxyl-2-yl and 2,4,4-trimethyl-imidazolidine-3-oxyl-2-yl, as a preferred mode.

Third Mode:

A block copolymer represented by the General Formula (III)

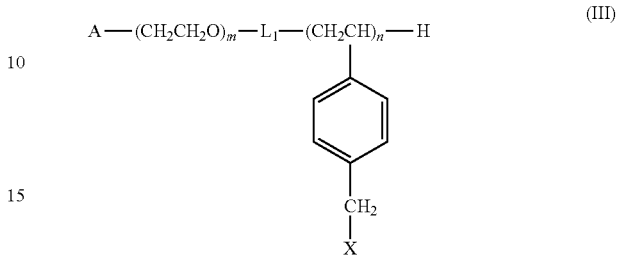

where A represents a non-substituted or a substituted $C_1$-$C_{12}$ alkoxy group, when substituted, the substituent represents a formyl group or a group of formula $R^1R^2CH$—, where $R^1$ and $R^2$ are independent and represent a $C_1$-$C_4$ alkoxy or $R^1$ and $R^2$ are combined and represent —OCH$_2$CH$_2$O—, —O(CH$_2$)$_3$O— or —O(CH$_2$)$_4$O—, $L_1$ represents a linking group selected from the group consisting of a valence bond, —(CH$_2$)$_c$S— and —CO(CH$_2$)$_c$S—, where c represents an integer from 1 to 5, X represents a chlorine, a bromine or an iodine atom, m represents an integer from 20 to 5,000 and n represents an integer from 3 to 1,000.

Fourth Mode:

A pharmaceutical composition for the prevention or the treatment of a disease or a symptom in which a reactive oxygen species or a hydroxy radical is involved, for instance, the group consisting of cerebral infarction, cardiac infarction, cerebral edema, neurological deficit, inflammation, hypertension, hyperlipidemia, obesity, cerebrovascular injury and neuronal cell damage, the composition comprising the polymerized nitroxide radical compound, preferably, a compound represented by the General Formula (II)

$$A-(CH_2CH_2O)_m-L_1-(CH_2CH)_n-H \quad (II)$$

(with phenyl group bearing $L_2$–X substituent)

where A represents a non-substituted or substituted $C_1$-$C_{12}$ alkoxy, when substituted, the substituent represents a formyl group or a group of formula $R^1R^2CH$—, where $R^1$ and $R^2$ are independent and represent a $C_1$-$C_4$ alkoxy or $R^1$ and $R^2$ are combined and represent —OCH$_2$CH$_2$O—, —O(CH$_2$)$_3$O— or —O(CH$_2$)$_4$O—, $L_1$ represents a linking group selected from the group consisting of a valence bond, —(CH$_2$)$_n$S—, —CO(CH$_2$)$_c$S—, where c represents an integer from 1 to 5, and preferably 2, $L_2$ represents a linking group selected from the group consisting of methylimino, methyliminomethyl, methyloxy, methyloxymethyl, methyl ester and methyl ester methyl, at least 50% of n in the total number of R represents a residue of cyclic nitroxide radical compound selected from the group consisting of 2,2,6,6-tetramethylpiperidine-1-oxyl-4-yl, 2,2,5,5-tetramethylpyrrolidine-1-oxyl-3-yl, 2,2,5,5-tetramethylpyrroline-1-oxyl-3-yl and 2,4,4-trimethyl-1,3-oxazolidine-3-oxyl-2-yl, 2,4,4-trimethyl-1,3-thiazolidine-3-oxyl-2-yl and 2,4,4-trimethyl-imidazolidine-3-oxyl-2-yl, and when present the remaining R represents a hydrogen atom, a halogen atom or a hydroxy group, m represents an integer from 20 to 5,000 and n represents an integer from 3 to 1,000, and a pharmaceutically allowed carrier.

Fifth Mode:

A reagent for detecting the presence of a reactive oxygen species or a free radical (or a hydroxy radical) in vivo, comprising the compound represented by the General Formula (II) and a pharmaceutically allowed carrier.

Sixth Mode:

A method for the prevention or the treatment of a disease or a symptom in which a reactive oxygen species or a free radical (or a hydroxy radical) is involved, for instance, cerebral infarction, cardiac infarction, cerebral edema, neurological deficit, inflammation, hypertension, hyperlipidemia, obesity, cerebral vascular injury and neuronal cell damage, comprising administering to a patient having a disease or a symptom in which a reactive oxygen species or a free radical (or a hydroxy radical) is involved, the compound represented by General Formula (II) at a dose that is effective for preventing or treating the disease or the symptom.

Although not to be limited by a theory, polymerized nitroxide radical compounds such as those described above, by self-assembling in an aqueous medium, form a polymeric micelle having a particle size of tens of nanometers in which it is assumed that nitroxide radical portions are maintained in the core region and the poly(ethylene glycol) strands are present in the shell region (regarding a conceptual drawing of the polymeric micelle, refer to the structure below high pH in FIG. 20). Such a polymeric micelle that encapsulates cyclic nitroxide radicals is maintained stably over a long period of time even in the presence of reducing species such as glutathione or ascorbic acid described above. In addition, if the cyclic nitroxide radical compounds are polymerized through an imino group by following the present invention, disruption of the polymeric micelle that encapsulates the cyclic nitroxide radicals is promoted under acidic pH conditions and radicals are released under the surrounding environment, such that an action that is intrinsic to the cyclic nitroxide radical (refer to Non-patent Reference 1 above) is performed. Therefore, it can be predicted that the action of the cyclic nitroxide radical may be exerted selectively at an inflammation site or the like, which in general is known to be in an acidic state. Consequently, since the polymerized nitroxide radical compound of the present invention eliminates effectively reactive oxygen species or reactive radical species at a diseased site, it is a novel material that not only allows expectations to be held in anti-inflammatory agent, blood pressure depressant, high fat blood plasma therapeutic drug, weight-reducing drug and the like, but also may become a completely novel drug the exhibits, for example, suppression of necrosis of normal cells in radiotherapy. In this way, the present invention provides a compound that holds expectation not only as a novel type-contrasting medium, but also as an oxidizing agent for a medical treatment that may regulate a redox reaction, for instance, a therapeutic agent for cerebral infarction, cardiac infarction, cerebral edema, neurological deficit, inflammation, hypertension, hyperlipidemia, obesity, cerebrovascular injury and neuronal cell damage, furthermore, a blood pressure depressant, an anti-inflammatory agent, and in addition, as an antioxidant or a supplement for food or the like.

DETAILED DESCRIPTION OF THE INVENTION

Figure 1:
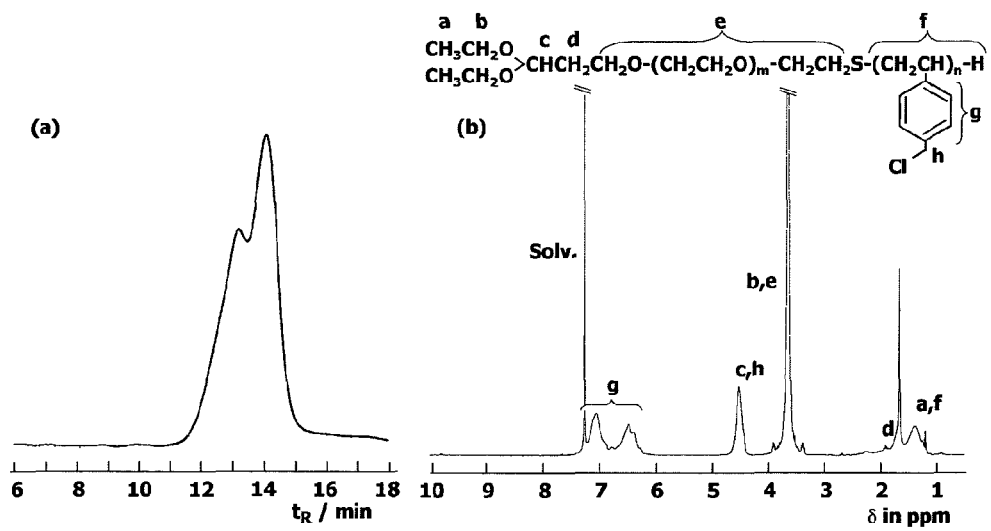
FIG. 1 is a graph showing the results of size exclusion chromatography (a) and $^1$H NMR spectrum of acetal-PEG-b-PCMS (b), a product obtained in Preparation Example 1.

With the stabilization method for cyclic nitroxide radical compound, which is the present invention of the First Mode, a cyclic nitroxide radical compound that can bond covalently with the hydrophobic segment of a block copolymer can stabilize a wide range of compounds without being limited to, for instance, so-called, stable nitroxide radical compounds, such as those advantageously used in spin labeling methods.

A block copolymer that can be used in such a stabilization method comprises, as stipulated above, a poly(ethylene glycol) chain segment (A) and a hydrophobic chain segment (B) carrying a reactive group, and is preferably a di-block copolymer of the AB type, but may also be a tri-block copolymer of the ABA type, or a tetra-block copolymer of the ABBA type. However, among such copolymers, as desirable ones, di-block copolymers may be cited, the block copolymer being represented by General Formula (I)

$$A\text{-}(CH_2CH_2O)_m\text{-}L_1\text{-}(h\text{-phobic})\text{-}Z \qquad (1)$$

where A represents a non-substituted or substituted $C_1\text{-}C_{12}$ alkoxy, when substituted, the substituent represents a formyl group or a group of formula $R^1R^2CH$— (where $R^1$ and $R^2$ are independent and represent a $C_1\text{-}C_4$ alkoxy or $R^1$ and $R^2$ are combined and represent —$OCH_2CH_2O$—, —$O(CH_2)_3O$— or —$O(CH_2)_4O$—), $L_1$ represents a linking group selected from the group consisting of a valence bond, —$(CH_2)_cS$—, —$CO(CH_2)_nS$—, —$(CH_2)_cNH$—, —$(CH_2)_cCO$— (where each c is an integer from 1 to 5, and preferably 1 or 2), —CO—, —COO— and —CONH—, (h-phobic) can be selected from those derived from polymers that are well known per se as biocompatible or medical polymers in the relevant technical field. Although not to be limiting, those represented by the following formulae can be given as concrete examples:

a poly amino acid ester chain segment represented by

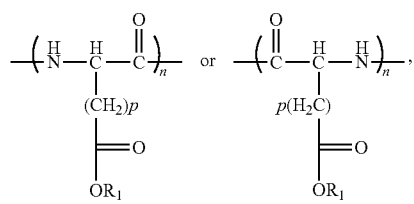

where p represents 1 or 2, $R_1$ represents a $C_1\text{-}C_{12}$ alkyl group optionally substituted at the nonbonding end with one phenyl group or benzhydryl group, and n represents an integer from 3 to 1,000, preferably from 5 to 500 and more preferably from 10 to 300;

a poly((meta) acrylic acid ester) chain segment represented by

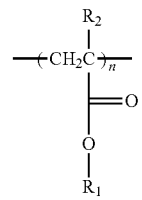

where $R_1$ represents a $C_1\text{-}C_{12}$ alkyl group optionally substituted at the nonbonding end with one phenyl group or benzhydryl group, $R_2$ represents a hydrogen atom or a $C_{1\text{-}5}$ alkyl group, preferably a methyl group, and n represents an integer from 3 to 1,000, preferably from 5 to 500 and more preferably from 10 to 300;

a styrene-maleic anhydride copolymer chain segment represented by

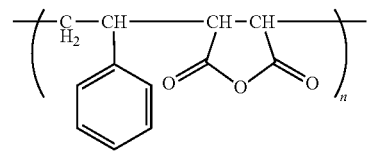

where n represents an integer from 3 to 1,000, preferably from 5 to 500 and more preferably from 10 to 300;

a poly malic acid ester chain segment represented by

where $R_1$ represents a $C_1\text{-}C_{12}$ alkyl group optionally substituted at the nonbonding end with one phenyl group or benzhydryl group, and n represents an integer from 3 to 1,000, preferably from 5 to 500 and more preferably from 10 to 300;

a poly amic acid chain segment represented by

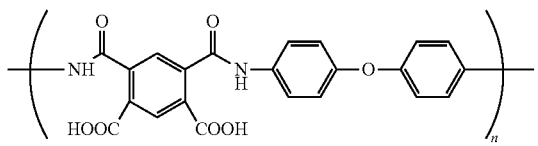

where n represents an integer from 3 to 1,000, preferably from 5 to 500 and more preferably from 10 to 300;

a poly maleimide chain segment represented by

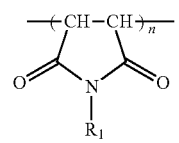

where $R_1$ represents a $C_1\text{-}C_{12}$ alkyl group optionally substituted at the nonbonding end with one phenyl group or benzhydryl group, and n represents an integer from 3 to 1,000, preferably from 5 to 500 and more preferably from 10 to 300;

a poly(halomethylstyrene) chain segment represented by

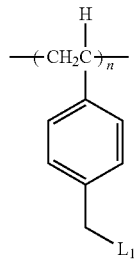

where $L_1$ represents a chlorine, bromine or iodine atom, and n represents an integer from 3 to 1,000, preferably from 5 to 500 and more preferably from 10 to 300;

a poly(vinyl chloride) chain segment represented by

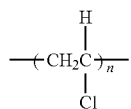

where n represents an integer from 3 to 1,000, preferably from 5 to 500 and more preferably from 10 to 300;

a poly(chloroprene) chain segment represented by

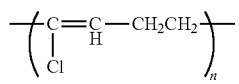

where n represents an integer from 3 to 1,000, preferably from 5 to 500 and more preferably from 10 to 300;

a poly(glycidylmethacrylate) chain segment represented by

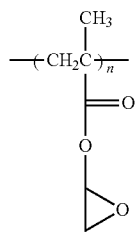

where n represents an integer from 3 to 1,000, preferably from 5 to 500 and more preferably from 10 to 300;

a poly(2-hydroxyethylmetacrylate) chain segment represented by

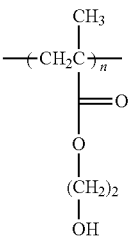

where n represents an integer from 3 to 1,000, preferably from 5 to 500 and more preferably from 10 to 300;

a poly(epichlorohydrin) chain segment represented by

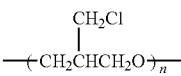

where n represents an integer from 3 to 1,000, preferably from 5 to 500 and more preferably from 10 to 300;

a poly(3,3-bischloromethyloxetane) chain segment represented by

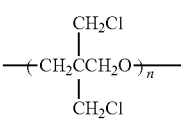

where n represents an integer from 3 to 1,000, preferably from 5 to 500 and more preferably from 10 to 300;

a poly(oxazoline) chain segment represented by

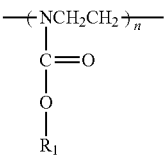

where $R_1$ represents a $C_1$-$C_{12}$ alkyl group optionally substituted at the nonbonding end with one phenyl group or benzhydryl group, and n represents an integer from 3 to 1,000, preferably from 5 to 500 and more preferably from 10 to 300;

a polysiloxane chain segment represented by

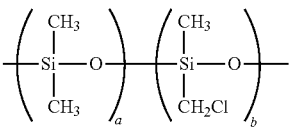

where a and b independently represent an integer from 3 to 500;

a poly(vinylphenyl boronic acid) chain segment represented by

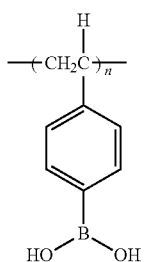

where n represents an integer from 3 to 1,000, preferably from 5 to 500 and more preferably from 10 to 300;

a 1-nylon chain segment represented by

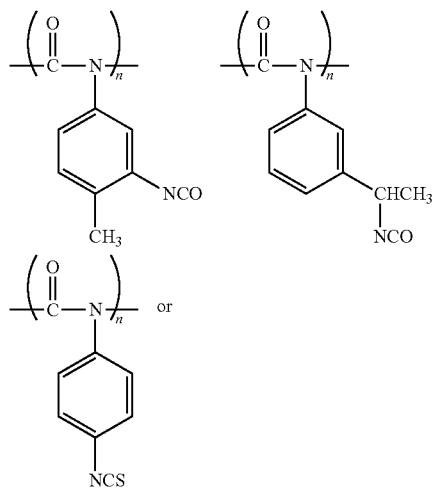

where each n represents an integer from 3 to 1,000, preferably from 5 to 500, and more preferably from 10 to 300; and a poly(vinyl benzaldehyde) chain segment represented by

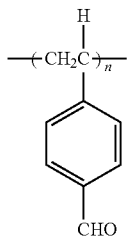

where n represents an integer from 3 to 1,000, preferably from 5 to 500 and more preferably from 10 to 300.

Moreover, in the above Formula (I),

Z represents a hydrogen atom, a hydroxy, a $C_1$-$C_{12}$ alkyloxy optionally substituted at the nonbonding end with one phenyl group or benzhydryl group or a $C_1$-$C_{12}$ alkyl carbonyl optionally substituted at the nonbonding end with one phenyl group or benzhydryl group.

However, in particular, a block copolymer in which the hydrophobic chain segment of the block copolymer carrying the reactive group is a poly(halomethylstyrene) chain segment of formula

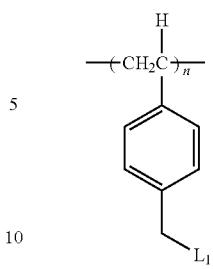

where $L_1$ represents a chlorine, bromine or iodine atom and n represents an integer from 3 to 1,000, can be used preferably.

A portion of such block copolymers is well known, for instance, those in which the hydrophobic segment represents a poly amino acid ester chain segment are well known through Japanese Patent No. 2690276 (U.S. Pat. No. 5,449,513) or the like, in addition, those representing a poly((meta)acrylic acid ester) chain segment through Patent Reference 3. Other block copolymers can be acquired readily for a person of ordinary skill in the art by referring to the block copolymer preparation method mentioned above or Preparation Example 1 described below in the present specification. Note that when a linking group or a repeating unit of the general formula defining the block copolymer used in the present invention is represented by a formula, it is intended to be integrated in the general formula with the depicted directionality.

Although a cyclic nitroxide radical can be used without limitation as long as it is one that can be stabilized by the method of the present invention, a cyclic nitroxide radical compound that is strongly planned for stabilization with the present invention is selected from the group consisting of 4-substituted 2,2,6,6-tetramethylpiperidine-1-oxyl, 3-substituted 2,2,5,5-tetramethylpyrrolidine-1-oxyl, 3-substituted 2,2,5,5-tetramethylpyrroline-1-oxyl, 2-substituted 2,4,4-trimethyl-1,3-oxazolidine-3-oxyl, 2-substituted 2,4,4-trimethyl-1,3-thiazolidine-3-oxyl and 2-substituted 2,4,4-trimethyl-imidazolidine-3-oxyl, the substituents of the 4-substitution, the 3-substitution or the 2-substitution being selected from the group consisting of the amino group, the aminomethyl group and the hydroxyl group, the hydroxymethyl group, the carboxyl group and the carboxymethyl group.

The method for forming a covalent bond through a functional group of the cyclic nitroxide radical compound other than the radical (for instance, an amino group, an aminomethyl group, a hydroxyl group, a hydroxymethyl group, a carboxyl group or a carboxymethyl group) and a reactive group of the block copolymer (a halogen atom, and in particular a chlorine, bromine or iodine atom, a carboxyl group, an isocyanate residue, an isothiocyanate residue, an ester residue, an acid anhydride residue, a boronic acid residue, a maleimide residue or an epoxy group) can be performed by condensation reaction, addition reaction, which are well known per se, or, for instance, regarding an ester residue, aminolysis through the functional group (amino group) of the cyclic nitroxide radical compound, or the like. Such reactions may be performed in an aqueous solvent (water and organic solvents that are miscible in water, for instance, lower alcohols, dioxane, dimethyl formamide, dimethyl sulfoxide, and the like may be included), in the presence of an organic base (trimethylamine, triethanolamine or the like) or an inorganic base (potassium carbonate, sodium carbonate, sodium hydroxide or the like), and other condensation agents well known in the relevant technical field, as necessary. For the block copolymer, although one that is per se capable of forming a polymeric micelle by self-assembling in an aqueous solvent can be used conveniently, if one may form a polymeric micelle in an aqueous solvent in a morphology where the cyclic nitroxide radical compound is covalently bonded, it can be used in the present invention.

In another mode of the present invention, a polymerized compound of cyclic nitroxide radical compound prepared by a cyclic nitroxide radical compound stabilization method using such block copolymers as those described above is provided. Although not to be limiting, as a preferred mode, a polymerized nitroxide radical compound is provided, comprising a poly(ethylene glycol) chain segment in which the repeating unit of ethylene glycol is 15 to 10,000 and a polystyrene chain segment in which the repeating unit of styrene is 3 to 3,000, and, at least 10%, preferably 30%, more preferably 50%, even more preferably 80% and particularly preferably 100% of the repeating units of styrene in the polystyrene chain segment, at position 4 of the phenyl group, a residue of cyclic nitroxide radical compound being covalently bonded through a linking group selected from the group consisting of —CH$_2$NH—, —CH$_2$NHCH$_2$—, —CH$_2$O—, —CH$_2$OCH$_2$—, —CH$_2$OCO— and —CH$_2$OCOCH$_2$—, when present, the remainder of the position 4 being a halogen atom, a hydrogen atom or a hydroxyl group and the cyclic nitroxide radical compound being selected from the group consisting of 2,2,6,6-tetramethylpiperidine-1-oxyl-4-yl, 2,2,5,5-tetramethylpyrrolidine-1-oxyl-3-yl, 2,2,5,5-tetramethylpyrroline-1-oxyl-3-yl and 2,4,4-trimethyl-1,3-oxazolidine-3-oxyl-2-yl, 2,4,4-trimethyl-1,3-thiazolidine-3-oxyl-2-yl and 2,4,4-trimethyl-imidazolidine-3-oxyl-2-yl. More concretely and more preferably, a polymerized nitroxide radical compound of General Formula (II) is provided

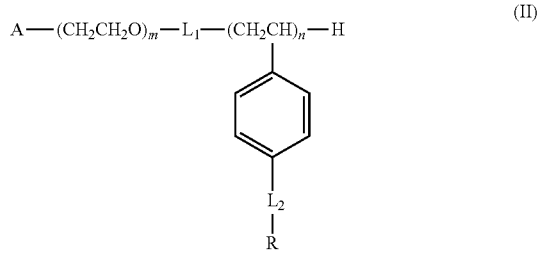

where A represents a non-substituted or substituted C$_1$-C$_{12}$ alkoxy, when substituted, the substituent represents a formyl group or a group of formula R$^1$R$^2$CH— (where R$^1$ and R$^2$ are independent and represent a C$_1$-C$_4$ alkoxy or R$^1$ and R$^2$ are combined and represent —OCH$_2$CH$_2$O—, —O(CH$_2$)$_3$O— or —O(CH$_2$)$_4$O—)

L$_1$ represents a linking group selected from the group consisting of a valence bond, —(CH$_2$)$_n$S—, —CO(CH$_2$)$_c$S—, where c is an integer from 1 to 5, and preferably 2, L$_2$ represents a linking group selected from the group consisting of methyl imino (—CH$_2$NH—), methyl iminomethyl (—CH$_2$NHCH$_2$—), methyloxy (—CH$_2$O—), methyloxymethyl (—CH$_2$OCH$_2$—), methyl ester (—CH$_2$OCO—) and methyl ester methyl (—CH$_2$OCOCH$_2$—), at least 50% of n in the total number of R, represents a residue of cyclic nitroxide radical compound selected from the group consisting of 2,2,6,6-tetramethylpiperidine-1-oxyl-4-yl, 2,2,5,5-tetramethylpyrrolidine-1-oxyl-3-yl, 2,2,5,5-tetramethylpyrroline-1-oxyl-3-yl and 2,4,4-trimethyl-1,3-oxazolidine-3-oxyl-2-yl, 2,4,4-trimethyl-1,3-thiazolidine-3-oxyl-2-yl and 2,4,4-trimethyl-imidazolidine-3-oxyl-2-yl, and when present, the remaining R represents a hydrogen atom, a halogen atom or a hydroxy group, m represents an integer from 20 to 5,000, preferably from 30 to 3,000 and more preferably from 40 to 1,000 and n representing an integer from 3 to 1,000, preferably from 5 to 500 and more preferably from 10 to 500. In addition, polymerized nitroxide radical compounds for which, in General Formula (II), L$_1$ is a valence bond or —CH$_2$CH$_2$S—, L$_2$ is methyl imino or methyl iminomethyl and the entirety of R are residues of cyclic nitroxide radical compound represented by any of the following formulae

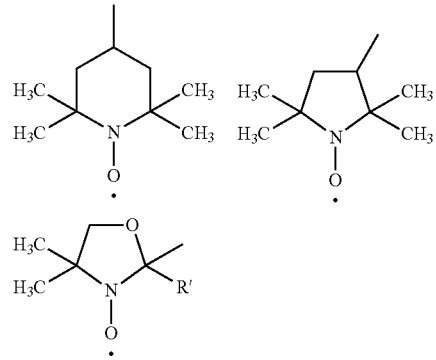

where R' is a methyl group,
are provided as a particularly desirable ones from the point of conferring pH responsiveness to the stabilization of the polymeric micelle that can be formed from these compounds.

In the definition of each group or portion described above, the alkyl portion of C$_1$-C$_{12}$ alkoxy can be straight or branched alkyl and, for instance, methyl, ethyl, propyl, iso-propyl, butyl, iso-butyl, s-butyl, t-butyl, pentyl, hexyl, heptyl, dodecanyl, and the like, can be cited. In addition, when A represents an alkoxy group substituted by formula R$^1$R$^2$CH—, and, R$^1$ and R$^2$ are independent and represent a C$_1$-C$_4$ alkoxy or R$^1$ and R$^2$ are combined and represent —OCH$_2$CH$_2$O—, —O(CH$_2$)$_3$O— or —O(CH$_2$)$_4$O—, since such a substituent can be readily cleaved under acidic condition and converted into a formyl group, proteins (for instance, antibodies and other ligands) or the like can be covalently bonded readily through an amino acid thereof. When present, it is desirable that such substituents be present at the non-bonded end of the alkoxy group. These substituent can be introduced for instance by referring to the poly(ethylene glycol) chain segment generation methods described in the above Patent References 2 and 3.

In addition, the linking group L$_1$ in the block copolymer described above is not limited, since it may be replaced according to how the poly(ethylene glycol) chain segment and polystyrene are to be bonded. For instance, when a poly(ethylene glycol) chain segment is generated by anionic living polymerization and then living polymerization of halomethylstyrene is continued, L$_1$ is a valence bond. When a poly(ethylene glycol) derivative having a sulphur atom at the ω-end of the poly(ethylene glycol) chain segment is prepared, by carrying out a radical polymerization of halomethylstyrene in the presence of the derivative, the linking group may be —CH$_2$CH$_2$S— or —COCH$_2$CH$_2$S—.

For $L_2$, typically, a linking group selected from the group consisting of methyl imino, methyl iminomethyl, methyloxy and methyloxymethyl, can be cited. While such a linking group varies conveniently depending on the halogen atom of the block copolymer, for instance, a block copolymer represented by General Formula (III)

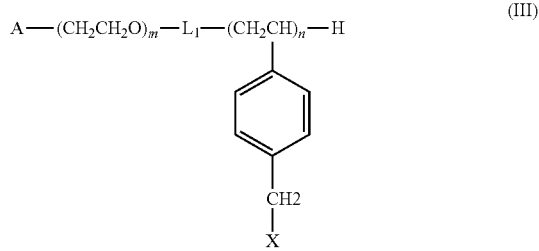

where A represents a non-substituted or substituted $C_1$-$C_{12}$ alkoxy, when substituted, the substituent represents a formyl group or a group of formula $R^1R^2CH$— (where $R^1$ and $R^2$ are independent and represent a $C_1$-$C_4$ alkoxy or $R^1$ and $R^2$ are combined and represent —$OCH_2CH_2O$—, —$O(CH_2)_3O$— or —$O(CH_2)_4O$—), $L_1$ represents a linking group selected from the group consisting of a valence bond, —$(CH_2)_nS$—, —$CO(CH_2)_cS$—, where c is an integer from 1 to 5, and preferably 2, X represents a chlorine, bromine or iodine atom, m represents an integer from 20 to 5,000 and n represents an integer from 3 to 1,000, and the species of the functional group other than the radical of the cyclic nitroxide radical compound, in general, it can be formed by a covalent bond formation reaction that accompanies the elimination of a hydrogen halide.

Note that, to the best of the present inventors' knowledge, the copolymer represented by General Formula (III) has not been described in the literature, and is provided as another mode of the present invention.

In General Formula (II), at least 50%, preferably at least 75%, more preferably at least 90% and particularly preferably 100% of n in the total number R represents a residue of cyclic nitroxide radical compound selected from the group consisting of 2,2,6,6-tetramethylpiperidine-1-oxyl-4-yl, 2,2,4,4-tetramethylpyrrolidine-1-oxyl-3-yl, 2,2,4,4-tetramethylpyrroline-1-oxyl-3-yl and 2,4,4-trimethyl-1,3-oxazolidine-3-oxyl-2-yl, 2,4,4-trimethyl-1,3-thiazolidine-3-oxyl-2-yl and 2,4,4-trimethyl-imidazolidine-3-oxyl-2-yl, and when present, the remaining R represents a hydrogen atom, a halogen atom or a hydroxyl group. The proportion occupied within n, the total number of R, by residues of cyclic nitroxide radical compound can be varied, for instance, by controlling the reaction between the copolymer of General Formula (III) described above and the cyclic nitroxide radical compound, for instance, by controlling the reaction time.

While described above, in addition, m can be an integer from 20 to 5,000, preferably from 35 to 3,000, and more preferably from 60 to 500 and n can also be an integer from 3 to 5000, preferably from 10 to 300, and more preferably from 15 to 100.

Since, as shown concretely in the Test Examples described below, even under reducing conditions, the polymerized nitroxide radical compound of the present invention demonstrates an action that is intrinsic to a cyclic nitroxide radical compound (for instance, refer also to Non-patent Reference 1), it can be used as an antioxidant inside and outside of an organism.

In the present specification, as a more concrete example of use of a compound stabilized by the methods described above, a compound described more concretely, can be used for prevention or treatment of a disease or a symptom in which a reactive oxygen species or a free radical (or a hydroxy radical) involved in vivo.

in vivo referred to in the present invention means inside the body of animals in general, humans to begin with, mammals, fishes and the like, and organs, viscera and body fluid can be cited.

There is no limitation on the diseases or symptoms in which a reactive oxygen species or hydroxy radical is involved, and cerebral infarction, cardiac infarction, cerebral edema, neurological deficit, inflammation, hypertension, hyperlipidemia, obesity, cerebrovascular injury and neuronal cell damage, more concretely, cerebral infarction, cerebral edema, and neurological deficit, cerebral infarction (in particular, atherothrombotic cerebral infarction, lacunar stroke, brain embolism), cerebrovascular spasm (in particular, transient cerebral artery constriction occurring after subarachnoidal bleeding), moyamoya disease (in particular, Willis' ring artery obstruction), brain major artery obstruction/stenosis and mesenteric vascular obstruction can be cited.

While a compound exerting an effect on such a disease or symptom can have as any of the above compounds as the active ingredient, a polymerized nitroxide radical compound can be cited, which, as a desirable one, is the compound represented by the above General Formula (II), and then, as a more desirable one, is a compound represented by the General Formula (II), where $L_1$ is a valence bond or —$CH_2CH_2S$—, $L_2$ is methyl imino or methyl iminomethyl and The entirety of R are residues of cyclic nitroxide radical compound represented by any of the following formulae

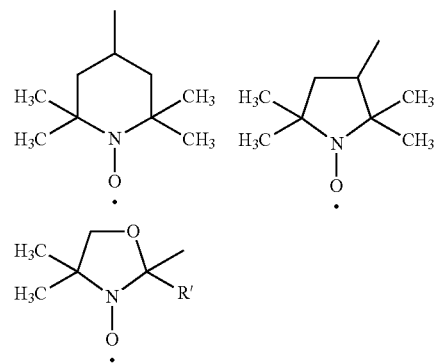

where, R' is a methyl group. When $L_2$ is methyl imino or methyl iminomethyl, disruption of the polymeric micelle that encapsulates the cyclic nitroxide radicals is promoted under acidic pH conditions and radicals are released under the surrounding environment, such that an action that is intrinsic to the cyclic nitroxide radical (refer to Non-patent Reference 1 above) is performed. Therefore, it can be anticipated that the action of the cyclic nitroxide radical may be exerted selectively at an inflammation site or the like, which in general is known to be in an acidic state.

As pharmaceutically acceptable diluents or excipients that can be included in the pharmaceutical composition, any can be cited as long as they are compounds or substances which are additives used ordinarily in the relevant technical field for preparing an injectable (intravenously and intraarterially injected agent), a locally administered agent (including embedding agent in brain) and the like, and which do not have a detrimental influence on the properties or function of the polymerized cyclic nitro radical. Not to be limiting, for injectables, pure water, deionized water or physiological saline may be cited typically as diluents, and buffering agent can also be included in these liquids. In addition, water miscible organic solvents such as ethanol and dimethylsulfoxide may be included in these liquids as long as they do not exert a detrimental influence on the stability of a polymeric micelle formed by the compound represented by General Formula (I). As excipients, sugars or sugar alcohols such as poly(ethylene glycol) (macrogol) of various molecular weights, glucose, lactose and mannitol, which are usable in drug formulation can be cited. As embedding agents in brain, for instance, those with a morphology where the compound is contained in the envelope matrix layer of a stent placed inside the brain can be cited. Referred herein, diluents or excipients (or carriers) that are acceptable in food can be based on those that are pharmaceutically acceptable described above.

Taking an intravenously administered agent as an example, the optimal dosage is not limited since it varies according to the patient's age, symptom, age, gender and the like; however, the dosage of the composition according to the present invention is, per day, from 0.1 to 900 mg/kg and preferably from 1 to 250 mg/kg based on the cyclic nitroxide radical compound in general with respect to an adult, and administration can be from once to three separate times.

Hereinafter, the present invention will be described in more in detail by giving concrete examples; however, they are not meant to limit the present invention is not intended to these modes.

Preparation Example 1

Synthesis of Poly(Ethylene Glycol)-b-Poly(Chloromethylstyrene) Having an Acetal Group at the α-End (Acetal-PEG-b-PCMS)

Acetal-PEG-b-PCMS was synthesized according to the following Synthesis Scheme 1:

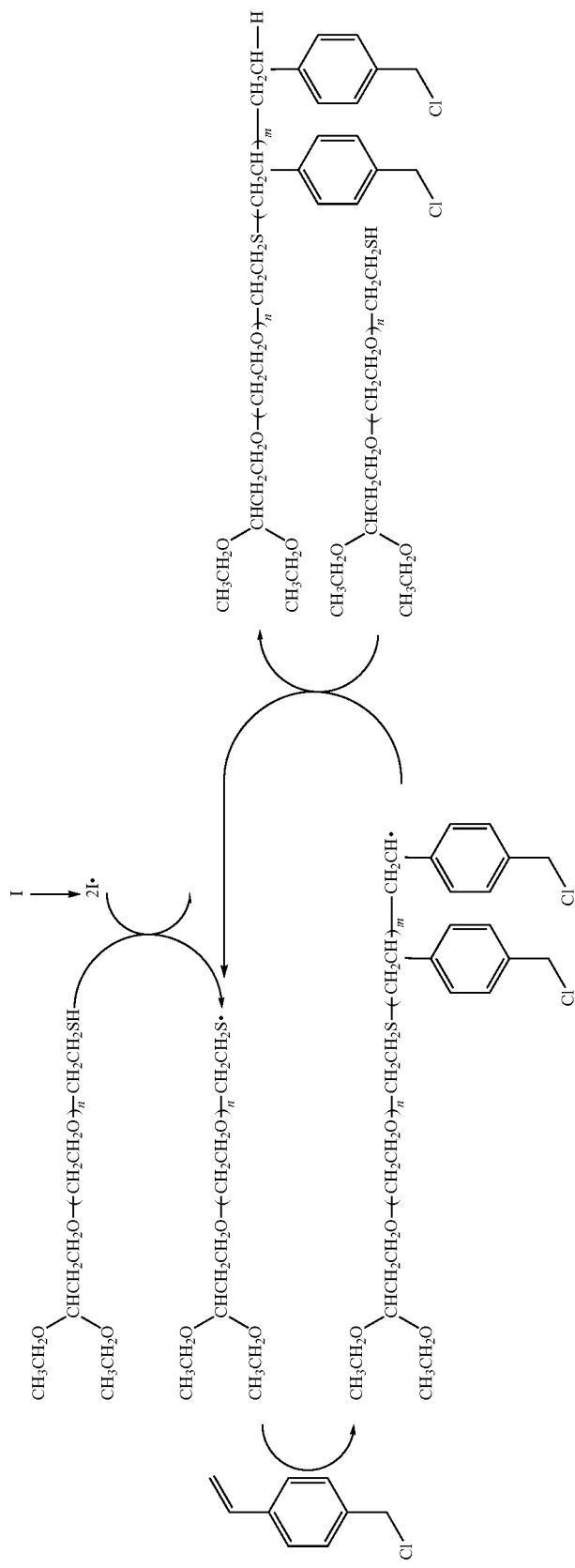

A heterobifunctional poly(ethylene glycol) (acetal-PEG-SH) (Mn: 4,600; 0.02 mmol, 92 mg) having an acetal group at the α-end and a thiol group at the ω-end was added to a reaction container. Next, the interior of the reaction container was turned into nitrogen atmosphere by repeating three times the operation of vacuuming the interior of the reaction container and blowing in nitrogen gas. To the reaction container, 1 mL of a solution of azobisisobutyronitrile/benzene (0.01 mmol/mL) and chloromethylstyrene (1 mmol, 0.138 mL), was added, heated to 60° C. and stirred for 24 hours. When the reaction mixture was poured into hexane, a white precipitation was generated. In order to eliminate poly(chloromethylstyrene) homopolymer, the obtained precipitate was put under washing operation three times using diethyl ether, which is a good solvent to poly(chloromethylstyrene) homopolymer, and then benzene freeze-drying was performed to obtain a white powder. The amount produced was 134 mg and the yield was 55.1%. A bimodal distribution was observed from the results of size-exclusion chromatography (SEC) measurements of the obtained acetal-PEG-b-PCMS block copolymer (FIG. 1a). In order to obtain information on the products, SEC was used to separate these two distributions, and the $^1$H NMR spectrum of the respective fraction was measured.

As a result, the component ratios for PEG and PCMS in the two fractions were found to be approximately equal. In addition, when the $^1$H NMR spectra were analyzed based on the molecular weight of acetal-PEG-SH determined by SEC in order to calculate the molecular weights of the PCMS segments within the obtained block copolymers, the molecular weights of the PCMS segments were found to be 3,300 and 6,600 respectively (FIG. 1b). From these results, the bimodal distribution was found to be a di-block copolymer product on one hand and a tri-block copolymer product on the other. This is suggests that a tri-block copolymer was generated by a mutual recombination of di-block copolymers in the course of telomerization. In addition, it was found by peak fitting that the constituent ratios of the di-block copolymer and the tri-block copolymer were 23% and 77%.

Preparation Example 2

Synthesis of Block Polymer Having TEMPO Bonded Through an Imino Bond (Acetal-PEG-b-PCMS-N-TEMPO)

Acetal-PEG-b-PCMS (Mn: 7,900; 40 mg, 5.2 µmol) was added to a reaction container. Next, 4-amino-TEMPO (88 mg, 520 mmol) was dissolved in 2 mL of dimethylsulfoxide (DMSO) and added to the reaction container, and stirring was performed at room temperature for 5 hours. After the end of the reaction, the reaction mixture was poured into 2-propanol, which had been cooled to −15° C., next, precipitation was performed three times using 2-propanol and then benzene freeze-drying was performed. The yield was 76.3%.

Figure 2:
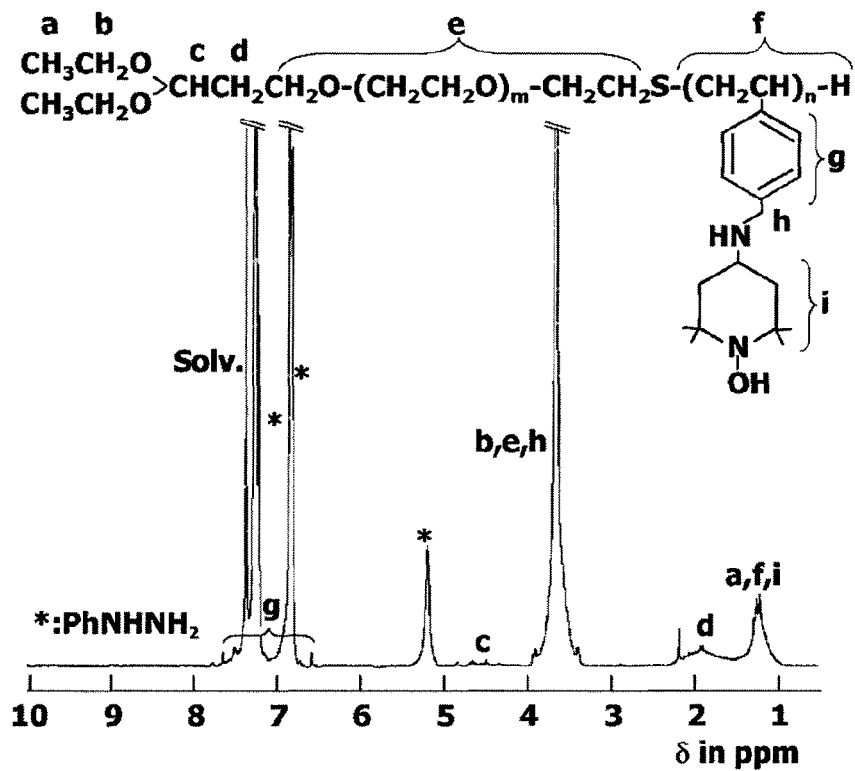
FIG. 2 is a $^1$H NMR spectrum of acetal-PEG-b-PCMS-N-TEMPO, a product obtained in Preparation Example 2.
Figure 3:
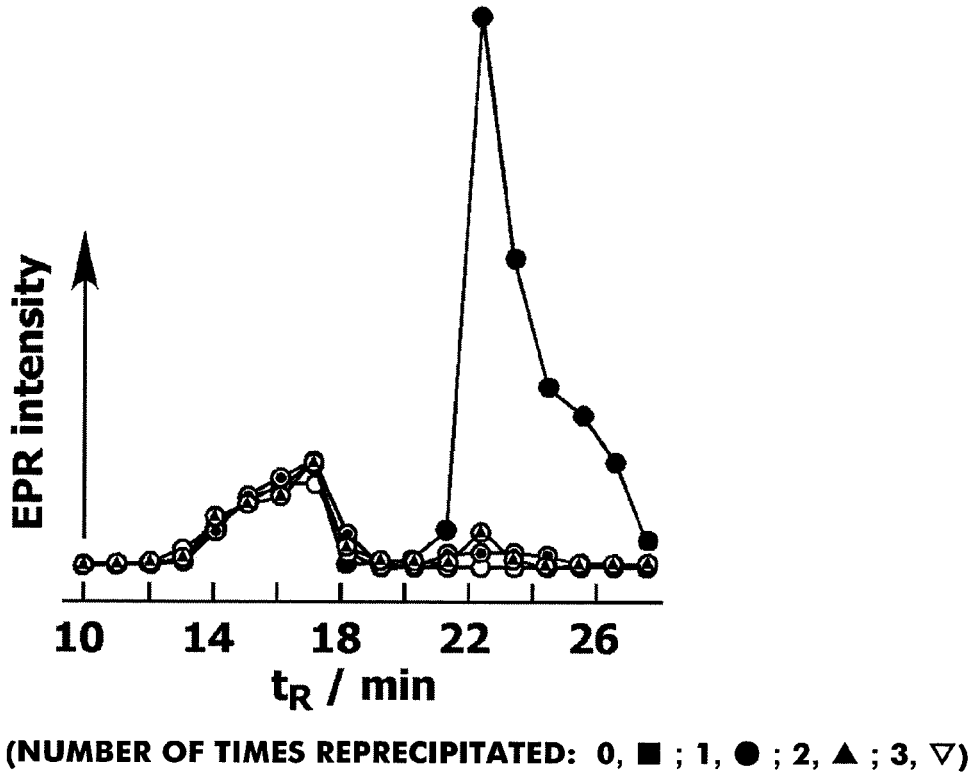
FIG. 3 is a graph representation showing the behavior, followed by ESR signal measurements, of non-reacted small molecule TEMPO being removed by purification of the reaction product of Preparation Example 2.

From the results of $^1$H NMR measurements, it was observed that 100% chloromethyl group reacted and TEMPO was introduced (FIG. 2). In addition, fractionation was performed using size-exclusion chromatography, and the ESR signal in each fraction was measured. As a result, from the fact that the ESR signal of non-reacted amino-TEMPO seen at 20 minutes to 27 minutes disappeared as the number of precipitations grew, it was verified that non-reacted amino-TEMPO was completely eliminated by purification (FIG. 3).

Preparation Example 3

Synthesis of Block Polymer Having TEMPO Bonded Through an Ether Bond (Methoxy-PEG-b-PCMS-O-TEMPO)

Methoxy-PEG-b-PCMS (Mn: 7,900; 200 mg, 30.6 µmol) was added to a reaction container and dissolved in 1 mL of dimethyl formamide (DMF). Next, 4-hydroxy-TEMPO (260 mg, 1.53 mmol) and NaH (70.3 mg, 3 mmol) were dissolved in 2 mL of DMF and added to the reaction container, and stirring was performed at room temperature for 5 hours. After the end of the reaction, the reaction mixture was poured into 2-propanol, which had been cooled to −15° C., next, precipitation was performed three times using 2-propanol and then benzene freeze-drying was performed to obtain the target methoxy-PEG-b-PCMS-O-TEMPO. The yield was 70.0%.

Preparation Example 4

Preparation of Nanoparticle from Acetal-PEG-b-PCMS-N-TEMPO(N-TEMPO-RNP)

Figure 4:
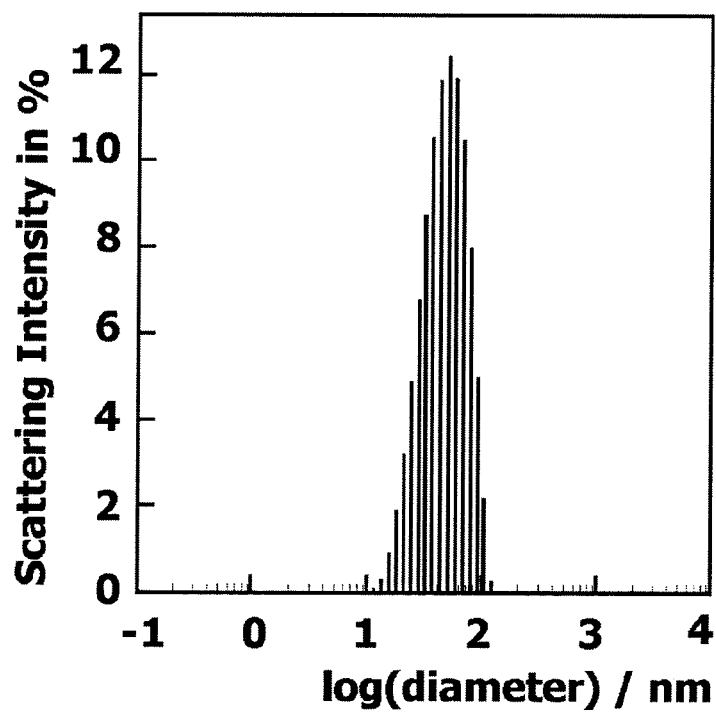
FIG. 4 is a figure showing the results of dynamic light scattering (DLS) measurements on the nanoparticle (N-TEMPO-RNP) from acetal-PEG-b-PCMS-N-TEMPO obtained in Preparation Example 3.
Figure 5:
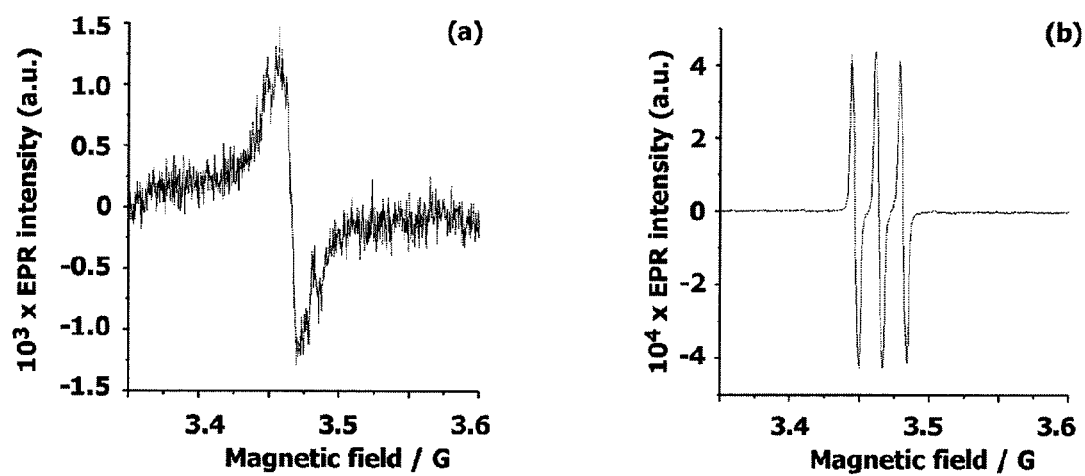
FIG. 5 is an ESR spectrum (a) of the nanoparticle from N-TEMPO-RNP obtained in Preparation Example 3 and an ESR spectrum (b) in a diluted solution of the small molecule TEMPO.

Dissolved in 2 mL of DMF was 20 mg of acetal-PEG-b-PCMS-N-TEMPO, and the polymer solution was added inside of a dialysis membrane (Spectra/Por; molecular weight cut-off size: 3,500; Spectrum Medical Industries Inc., Houston, Tex.) to perform dialysis against 2 L of distilled water. The distilled water was exchanged three times after 2, 4 and 8 hours. After the dialysis, when the average particle size of the obtained RNP was measured by DLS measurements, it was verified to be a monomodal particle with an average particle size of 40 nm (FIG. 4). Next, measurements of ESR spectra were performed for the obtained N-TEMPO-RNP. While in general the small molecule TEMPO in a dilute solution demonstrates a spectrum with three lines due to the interaction between the nitrogen nucleus and the unpaired electrons (FIG. 5b), the N-TEMPO-RNP prepared with acetal-PEG-b-PCMS-N-TEMPO was found to demonstrate a spectrum with one broad line (FIG. 5a). It is believed that by forming a solid phase in which the hydrophobic PCMS-TEMPO segment is aggregated as a particle core, the mobility of TEMPO decreased and, furthermore, the distance between TEMPOs became shorter, which increased the line width in the spectrum and resulted in the spectrum changing from three lines to one line.

Preparation Example 5

Preparation of Nanoparticle from Methoxy-PEG-b-PCMS-O-TEMPO (O-TEMPO-RNP)

Except that acetal-PEG-b-PCMS-N-TEMPO in Preparation Example 4 was changed to methoxy-PEG-b-PCMS-O-TEMPO, the operation procedure of Preparation Example 4 was repeated using similar amounts of reactants, solvents, and the like. When DLS measurements were performed in order to confirm the average particle size of O-TEMPO-RNP obtained in this way, it was verified to be monomodal with an average particle size of 40 nm, similarly to N-TEMPO-RNP of Preparation Example 4. Next, a measurement of ESR spectrum of the obtained O-TEMPO-RNP was performed. While in general the small molecule TEMPO in a dilute solution demonstrates a spectrum with three lines due to the interaction between the nitrogen nucleus and the unpaired electrons (refer to FIG. 5b above), O-TEMPO-RNP was observed to demonstrate a spectrum with one broad line similar to N-TEMPO-RNP shown in FIG. 5*a*. The cause for this is thought to be similar to those described regarding N-TEMPO-RNP.

Test 1: pH-Responsiveness of N-TEMPO-RNP and O-TEMPO-RNP

The average particle size and ESR spectra versus pH change for N-TEMPO-RNP obtained in Preparation Example 4 were measured by dynamic light scattering (DLS) and ESR. It was revealed that while in the region from neutral pH to basic pH the particles were monomodal with an average particle size of 40 nm and there was no change in the scattered intensity, in the acidic region, the scattered intensity decreased and the particle size increased. In addition, it was revealed by ESR measurements that, while at neutral pH and at basic pH the ESR spectrum of RNP was one broad line, under acidic conditions, the shape of the spectrum changed from one line to three lines (top of FIG. 6). The reasons for this is believed to be that, due to protonation of an amino group present on the hydrophobic segment branched chain of the block polymer, the particle is disrupted, furthermore, electrostatic repulsion occurs between the branched chains, increasing the mobility of TEMPO and, in addition, increasing the distance between TEMPOs.

Figure 6:
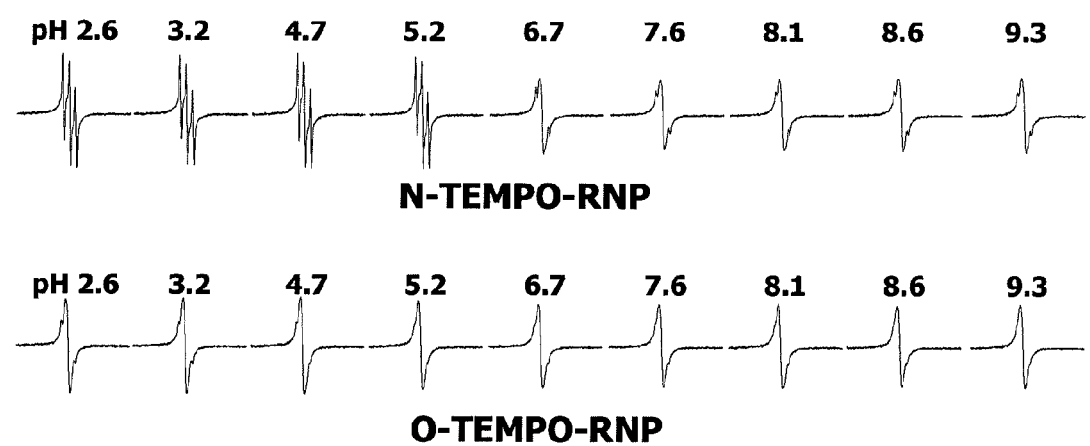
FIG. 6 shows the variation in the ESR spectrum accompanying a change in the pH of an micellar aqueous solution of N-TEMPO-RNP and O-TEMPO-RNP.

In contrast, O-TEMPO-RNP demonstrates similar ESR signals at all pH regions (bottom of FIG. 6).

Test 2: Reduction-Resistance of N-TEMPO-RNP Radical Against Glutathione

Figure 7:
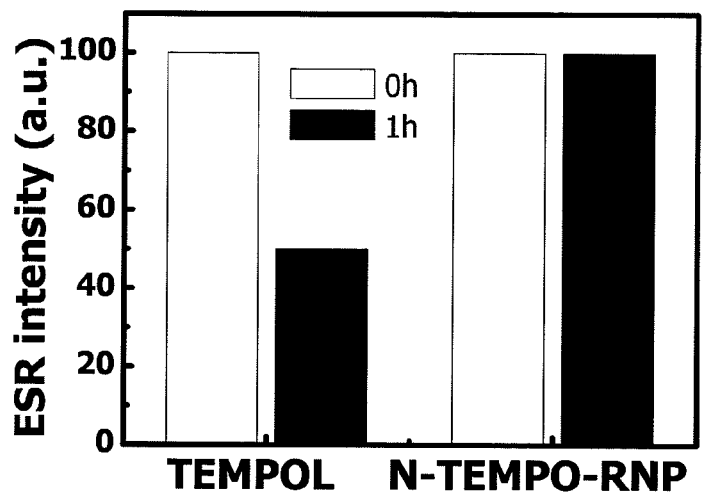
FIG. 7 is a graph representation of the results of a reduction-resistance test with glutathione for TEMPOL in N-TEMPO-RNP and the small molecule TEMPO.

It is known that, in general, while the interior of a cell is a reductive environment with high concentrations (0.5 mM to 10 mM) of glutathione present, on the order of only one over 100 to 1000 of that in the cell is present in blood. Thus, the small molecule TEMPO, which possesses a stable radical, is readily reduced upon entering inside a cell, rapidly loosing the ESR signal intensity. Then, in order to evaluate the glutathione reduction-resistance of the polymerized cyclic nitroxide radical, a solution of 64 µM of micelle comprising acetal-PEG-b-PCMS-N-TEMPO(N-TEMPO-RNP) was prepared (pH7.2) using a 900 mM Britton-Robinson buffer solution, and the change in the ESR spectrum was observed in the presence of 10 mM of glutathione. One hour after colocalization with GSH, a decrease of 50% was observed in the intensity of the ESR signal for the small molecule TEMPO (gray bar); in contrast, no change in the ESR signal intensity was observed for the prepared RNP (FIG. 7). From this result, it is believed that TEMPO present inside the core of the nanoparticle is stable against GSH present on the outside and thus could maintain a strong ESR signal intensity.

Test 3: Reduction-Resistance of N-TEMPO-RNP Radical Against Ascorbic Acid (AsA)

Figure 8:
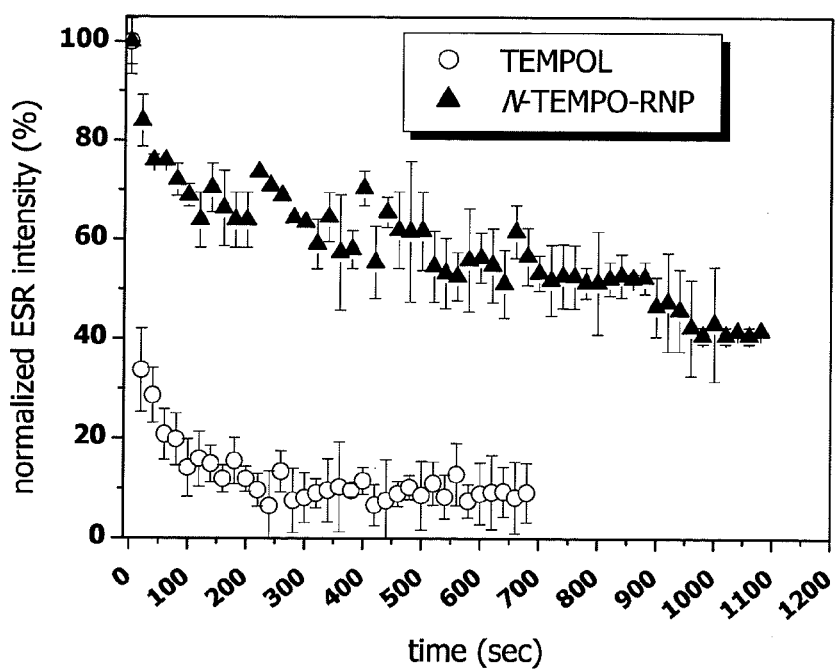
FIG. 8 is a graph representation of the results of a reduction-resistance test with ascorbic acid for TEMPOL in N-TEMPO-RNP and the small molecule TEMPO.

AsA, also referred to as vitamin C, is present in general at high concentrations in blood. The small molecule TEMPO, which possesses a stable radical, is known to be reduced readily in blood after intravital administration and decrease ESR signal intensity rapidly. Thus, in order to evaluate the reduction-resistance of N-TEMPO-RNP against AsA, the change in ESR spectrum of 90 µM of acetal-PEG-b-PCMS-N-TEMPO-prepared N-TEMPO-RNP was observed in the presence of 3.6 mM AsA, in a PBS buffer solution (10 mM, 150 mM NaCl, pH 7.4). The results are shown in FIG. 8. From the figure, it is clear that, in contrast to the half-life of the small molecule TEMPO being within 20 seconds, the half-life of N-TEMPO-RNP is approximately 15 minutes (the half-life increased approximately 45-folds).

Test 4: In-Blood Retention of N-TEMPO-RNP and O-TEMPO-RNP

Figure 9:
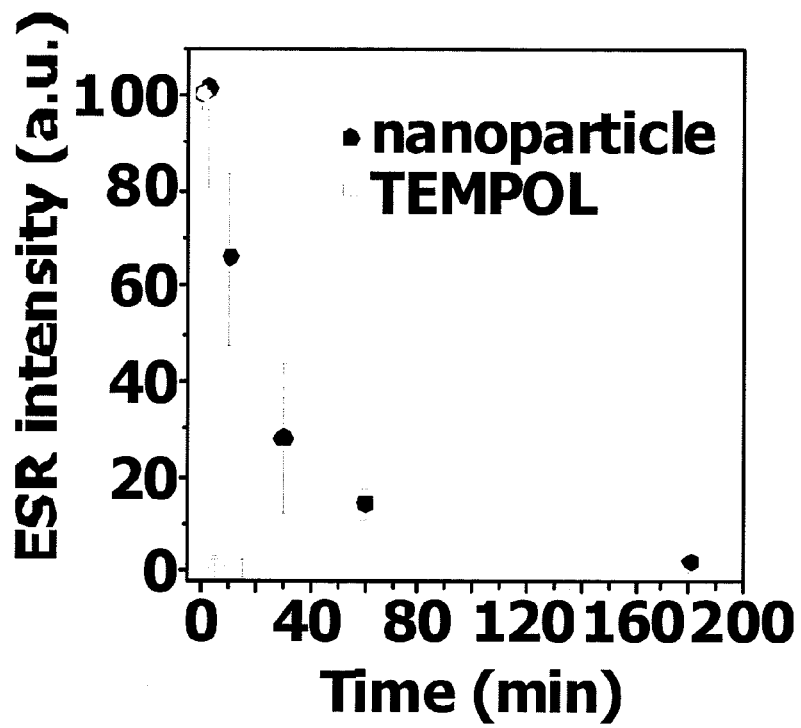
FIG. 9 is a graph representation of changes in blood concentration showing the results of disposition for TEMPOL in N-TEMPO-RNP and the small molecule TEMPO.
Figure 10:
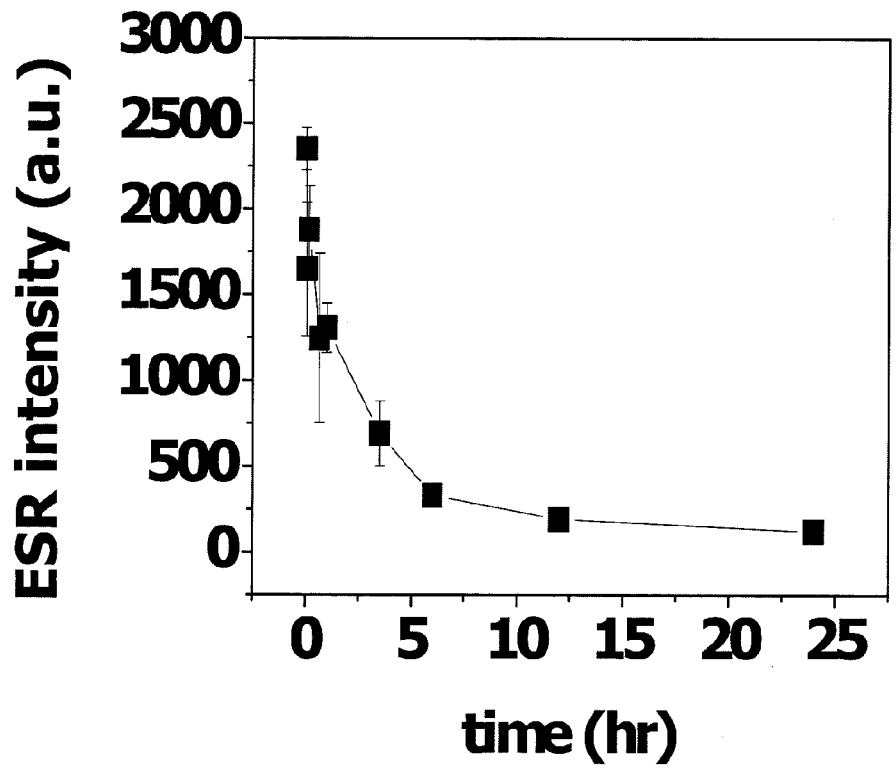
FIG. 10 is a graph representation of changes in blood concentration showing the results of disposition for O-TEMPO-RNP.

Each of N-TEMPO-RNP and O-TEMPO-RNP prepared as described above was independently injected in the vein of a different mouse, and after a given time period, laparotomy was performed to carry out blood collection from the heart. After blood collection, centrifugal separation was performed at 6,200 rpm (2000×g) for 10 minutes to obtain blood plasma. When the ESR spectrum of the obtained blood plasma was measured, an ESR signal of each RNP was observed from within the blood. In addition, when the disposition thereof was examined, the half-life was approximately 20 minutes for the former (FIG. 9) and approximately one hour for the latter (FIG. 10). It was revealed that N-TEMPO-RNP, which demonstrates pH responsiveness, has extremely higher in-blood stability than the in-blood half-life of the small molecule TEMPOL used as a control (<1 minute), while for O-TEMPO-RNP, which demonstrates no pH response, in-blood stability increased further.

Test 5: Treatment of Cerebral Ischemia Model Rat (1) Instead of acetal-PEG-SH used in the preparation of acetal-PEG-b-PCMS of Preparation Example 2, methoxy-PEG-SH was used to prepare methoxy-PEG-b-PCMS similarly, which served as raw materials for operating according to Preparation Examples 3 and 4 to obtain a polymer solution of methoxy-PEG-b-PCMS-N-TEMPO in dimethyl formamide, which was dialyzed and then, when the average particle size of the obtained RNP (N-TEMPO-RNP) was measured by DLS measurement, monomodal particles with an average particle size of 60 nm were observed. Physiological saline was added to the N-TEMPO-RNP aqueous solution obtained in this way, which was concentrated with a centrifugal evaporator so as to have a concentration of 100% physiological saline and adjusted to 20 mg/mL.

Cerebral ischemia model rats were prepared as follows:

SD strain male rats (3 weeks-old) were acclimatized for one week, and then inhalation anesthesia by isoflurane was performed. The common carotid artery was constricted with an occluding string and recirculated two hours after. Immediately after reperfusion, N-TEMPO-RNP (20 mg/mL) was injected from the femoral vein (or common carotid artery) at a concentration of 120 mg/mL and a rate of 1 mL/min. After 24 hours, they were sacrificed by Nembutal injection anesthesia. The brain was removed, the surface was hardened with liquid oxygen or dry ice, then, sliced to 2 mm thickness, and both sides were stained with a 2,3,5-triphenyl tetrazolium chloride (TTC) solution at 37 degrees, 30 minutes each. As controls, tests were also performed in parallel for a group in which no administration was performed after reperfusion and a group administered with Tempol at the same molar concentration as TEMPO in the polymerized TEMPO micelle (also called N-TEMPO-RNP). Each trial number was N=3.

Figure 11:
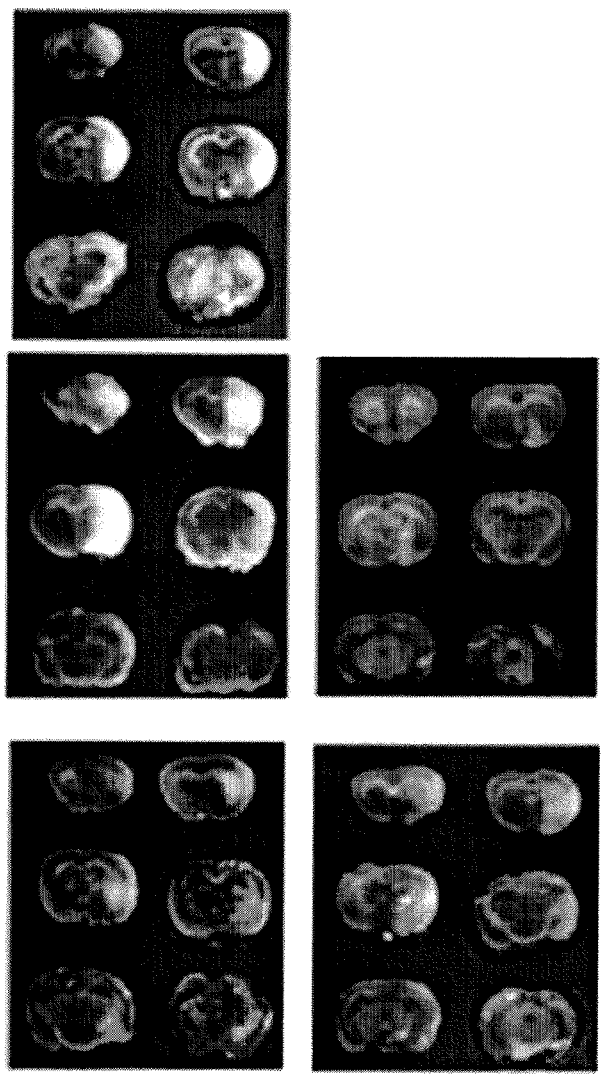
FIG. 11 is a TTC staining photograph of cerebral sections in Test 5. Respectively, the top row is the non-treated control group, the middle row is the Tempol-treated group, the bottom row is the N-TEMPO-RNP micelle-treated group, the photographs on the left side in the middle row and the subsequent row are for the vein-administered group, and the photographs on the right side are for the artery-administered group.

Examples of TTC-stained brain photographs are shown in FIG. 11. Portions stained in red (represented as black shades in the figure) are living cells and white portions are dead cells. In the intravenously administered N-TEMPO-RNP group, the red portions clearly increased compared to the non-treated group, and cell death was significantly prevented and this tendency was found to be prominent particularly in the penumbra region, which is told to be the drug treatment region in case of cerebral ischemia. In addition, with Tempol, more effect than N-TEMPO-RNP was not observed in the intravenously administered group. This is thought to be due to Tempol being reduced by a reductive constituent in the blood, by administering intravenously. It is assumed that, by polymerizing and enabling micelle formation, TEMPO was subjected to a degree of protection from the external environment of the organism.

Meanwhile, with arterial administration, more cell death-protection effect at a given level or greater was obtained than with intravenous administration, also with Tempol. This is thought to be due to the fact that with arterial administration, Tempol reaches the diseased site before being reduced by a blood circulating component. In addition, it is thought to be due to the fact that, in the case of venous administration, by being carried by the bloodstream and dispersed inside the body, the amount reaching the affected area is fewer than with administration from the common carotid artery.

Figure 12:
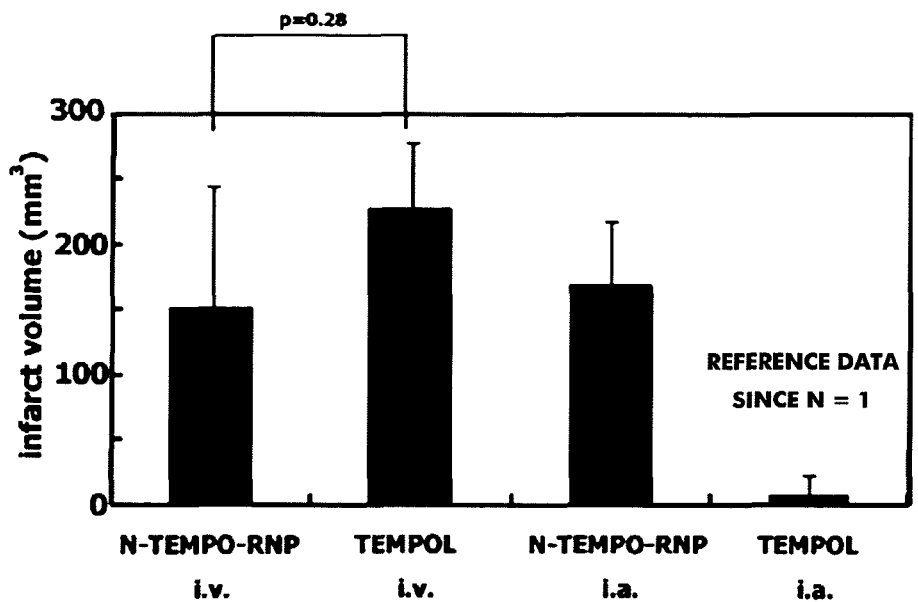
FIG. 12 is a graph representation of the results of quantification of the surface area of the infarcted portion (infract volume) in the results of TTC staining in Test 5, and Tempo micelle (C) iv and ia are groups administered respectively intravenously and intraarterially with a solution of nanoparticle, and Tempo iv and ia are a group and a subject administered respectively intravenously with a solution of Tempol.
Figure 13:
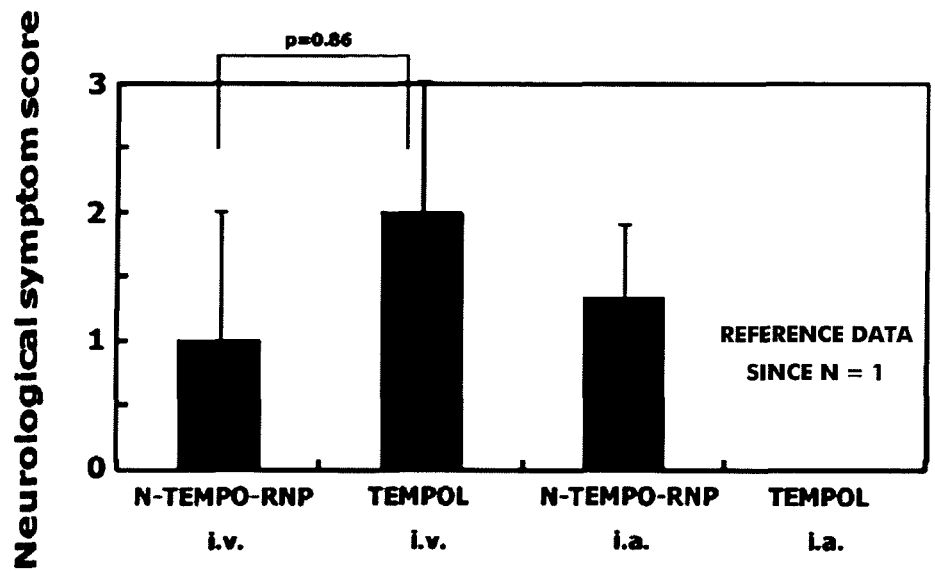
FIG. 13 is a graph representation of the neurological symptom score quantifying the symptoms of cerebral infarction in Test 5.

In addition, the surface area of the infarcted portion (infract volume) was quantified in the results of TTC staining and shown in FIG. 12 (N=3). From the figure, it was found that the infarction surface area has a tendency to decrease for venous N-TEMPO-RNP, in contrast to the veinously administered Tempol group. In addition, a similar tendency was also obtained with the neurological symptom score, which quantifies the symptom of cerebral infarction (Neurological symptom score=0: both anterior limbs are extended, no defects; 1: left anterior limb is on the chest and the right anterior limb is extended; 2: in addition to score 1, resistance to lateral push is decreased; 3: in addition to score 2, upper half body is twisted; the larger these values, the more severe the symptoms; FIG. 13), and a correlation was observed, that the more cerebral infarction surface areas there are, the more severe the symptoms.

(2) Tests were performed on cerebral ischemia model rats such as those described above, with additional trial numbers and controls or comparative examples.

The agents or controls the tests were performed with were as follows: performed with the above-mentioned N-TEMPO-RNP, a group with nothing administered after reperfusion as control, a group administered with Tempol at the same molar concentration as TEMPO in N-TEMPO-RNP, a group administered with 100% physiological saline and a group of micelle of methoxy-PEG-b-PCMS with no TEMPO added (hereinafter also referred to as Blank-NP; prepared according to Preparation Example 4) also in parallel. The respective test number N was N=20 for N-TEMPO-RNP and Tempol, and N=8 for physiological saline and Blank-NP. Analyses of body temperature, blood pressure and blood gas of the rat during operation were performed. The change in body weight between prior to model preparation and prior to sacrifice was also examined.

Figure 14:
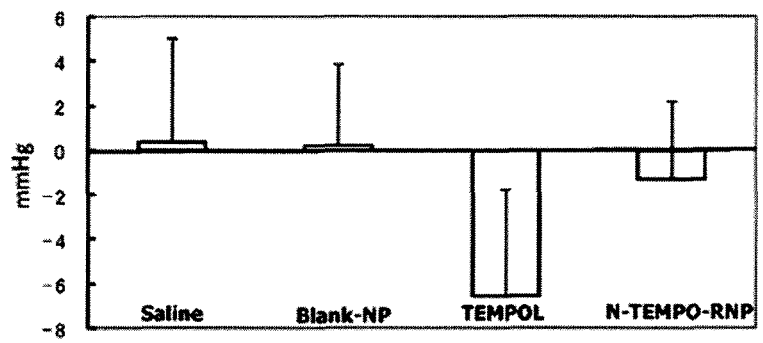
FIG. 14 is a graph representation of the results of variation in average blood pressure at agent administration time for physiological saline (Saline), Blank-NP and N-TEMPO-RNP in Test 5 (2).

No large differences were observed in the body weight change in each group before and after the test. In addition, difference was observed in the results of body weight and blood gas analyses, confirming that model preparation for each group was performed under a given condition. Average blood pressure at the time of agent administration decreased significantly for Tempol (refer to FIG. 14). Tempol is known to have hypotensive action, and generally, a blood pressure decreasing at the time of cerebral ischemia is an adverse effect in terms of treatment. However, blood pressure drop was significantly suppressed with N-TEMPO-RNP (p<0.01). This is thought to be the fact that blood pressure decreases due to the nitroxide radical in Tempol working for vasodilatation at administration time, while, the nitroxide radical is protected at administration time by polymer-micellization. To this extent, the nitroxide radical is thought to be usable for effectively eliminating free radicals in the brain.

Figure 15:
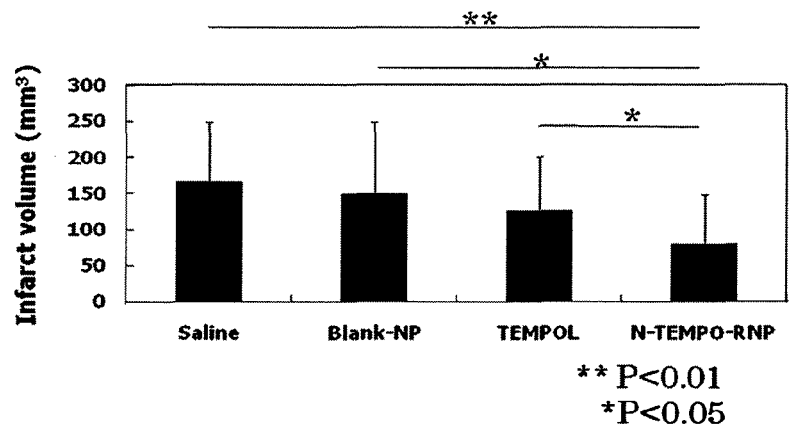
FIG. 15 is a representation of the results of quantification of the surface area of the infarcted portion (infract volume) in the results of TTC staining in Test 5 (2).

Regarding the cerebral infarction surface area (infract volume), N-TEMPO-RNP decreased the cerebral infarction surface area significantly compared to physiological saline, Blank-NP and Tempol (FIG. 15, p<0.01, 0.05, 0.05, respectively). The high brain protection effect of N-TEMPO-RNP compared to Tempol is though to be due to stable radical being maintained and translocated to the affected area by polymer-micellization.

Figure 16:
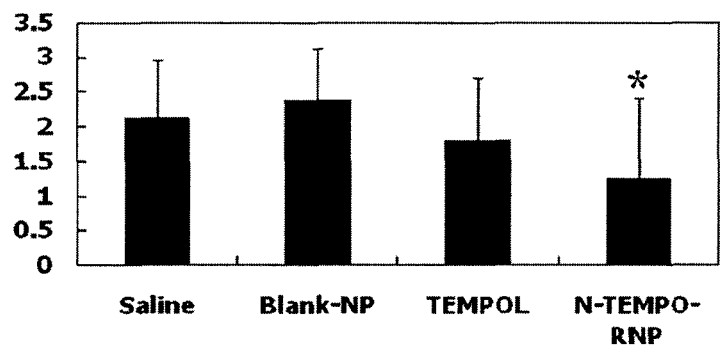
FIG. 16 is a graph representation of the neurological symptom score quantifying the symptoms of cerebral infarction in Test 5 (2).

Also with the neurological symptom score (0: when the tail is held and raised, both anterior limbs are extended, no defects; 1: when the tail is held and raised, left anterior limb is on the chest and the right anterior limb is extended; 2: in addition to score 1, resistance to lateral push is decreased; 3: in addition to score 2, upper half body is twisted; the larger these values, the more severe the symptoms), N-TEMPO-RNP decreased neurological symptoms more significantly than Tempol (refer to FIG. 16). In addition, there were no significant differences among physiological saline, Blank-NP and Tempol.

Test 6: Preparation of ESR Probe for the Purpose of Visualizing Reactive Oxygen Species (ROS) in a Cancerous/Inflammatory Tissue It has become apparent that oxidative stress induced by reactive oxygen species (ROS) is causes of various disorders and diseases. For instance, it is known that ROS is produced in cancerous tissues and inflammatory tissues. Visualization of ROS in vivo is extremely important for elucidating the relation ship between ROS and a disease. ESR imaging has been drawing attention in recent years as a tool for visualizing oxidation-reduction reaction in vivo. While various probes for ESR imaging have been developed so far, small molecule ESR probes have a short half-life in blood, in addition have no function for accumulating specifically a the target site, such that observation at a specific tissue is difficult. In addition, it is known that the pH is decreased in inflammation sites and cancerous tissues where oxidative stress are thought to be involved. Thus, exploiting the fact that N-TEMPO-RNP is disrupted under acidic conditions, the possibility of developing a ROS visualizable novel ESR probe was examined.

(1) Development of ROS Visualizable ESR Probe (N-TEMPO-RNP-H)

Figure 17:
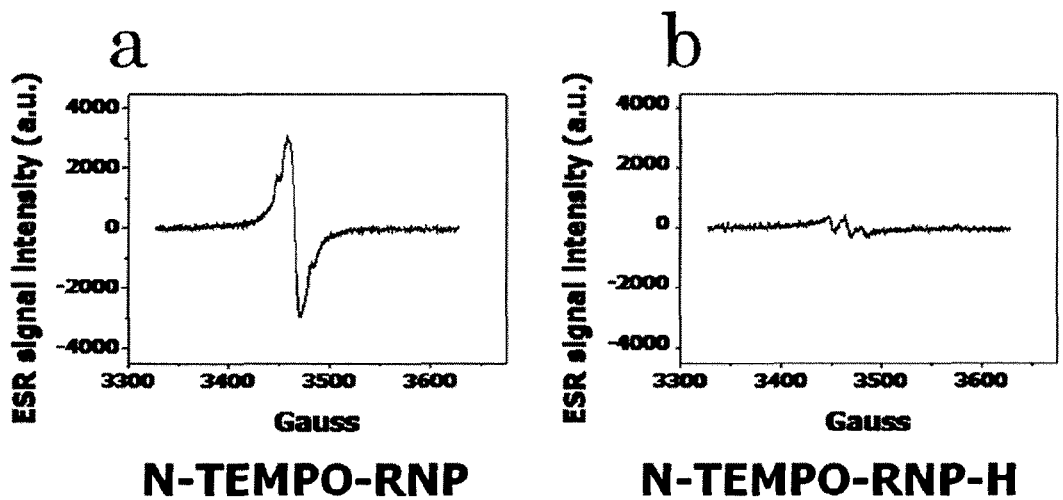
FIG. 17 is an ESR spectrum of N-TEMPO-RNP and hydrazine-reduced RNP (N-TEMPO-RNP-H).

To a DMF solution of 5 mg/mL methoxy-PEG-b-PCMS-N-TEMPO, 1500-fold in amounts of anhydrous hydrazine was added, the polymer solution was added inside a dialysis membrane (Spectra/Por; molecular weight cut-off size: 3,500; Spectrum Medical Industries Inc., Houston, Tex.) and a dialysis was performed against 2 L of distilled water. The distilled water was exchanged three times after 2, 4 and 8 hours. After the dialysis, when the average particle size of the obtained RNP was measured by DLS, it was verified to be a monomodal particle with an average particle size of 40 nm (similarly to the preparation of the nanoparticle (N-TEMPO-RNP) from acetal-PEG-b-PCMS-N-TEMPO according to Preparation Example 4). measurements of ESR spectra were performed for the RNP obtained in this way. While RNP demonstrated a spectrum with one broad line when no anhydrous hydrazine was added (FIG. 17*a*), it was found that when hydrazine was added, it changed to a spectrum with an extremely small intensity (FIG. 17*b*). This is believed to be due to the ESR signal intensity decreasing owing to the TEMPO radical being reduced by hydrazine.

(2) Model Experiment of Visualization of In Vivo Oxidation Reaction

Figure 18:
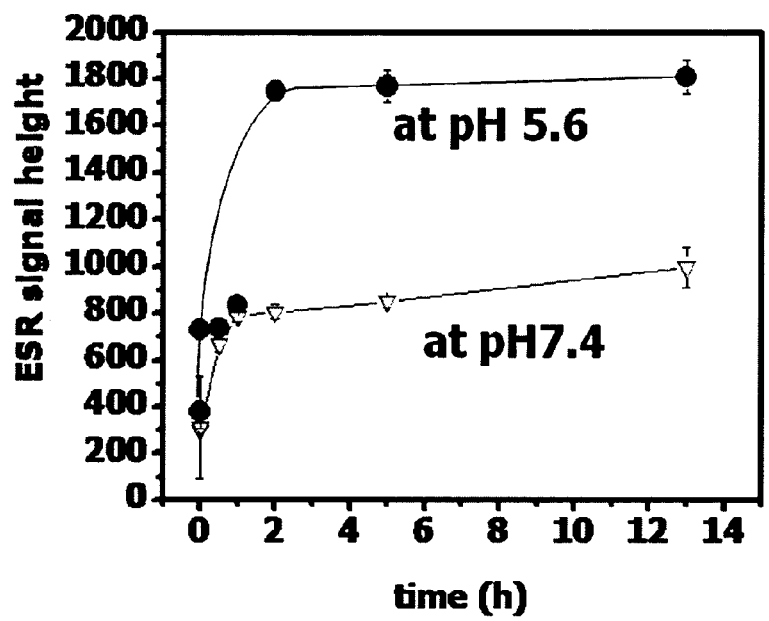
FIG. 18 is a graph representation of the variation over time of the ESR signal intensity for hydrazine-reduced RNP (N-TEMPO-RNP-H) observed in an oxidizing environment at pH 5.6 and pH 7.4.
Figure 19:
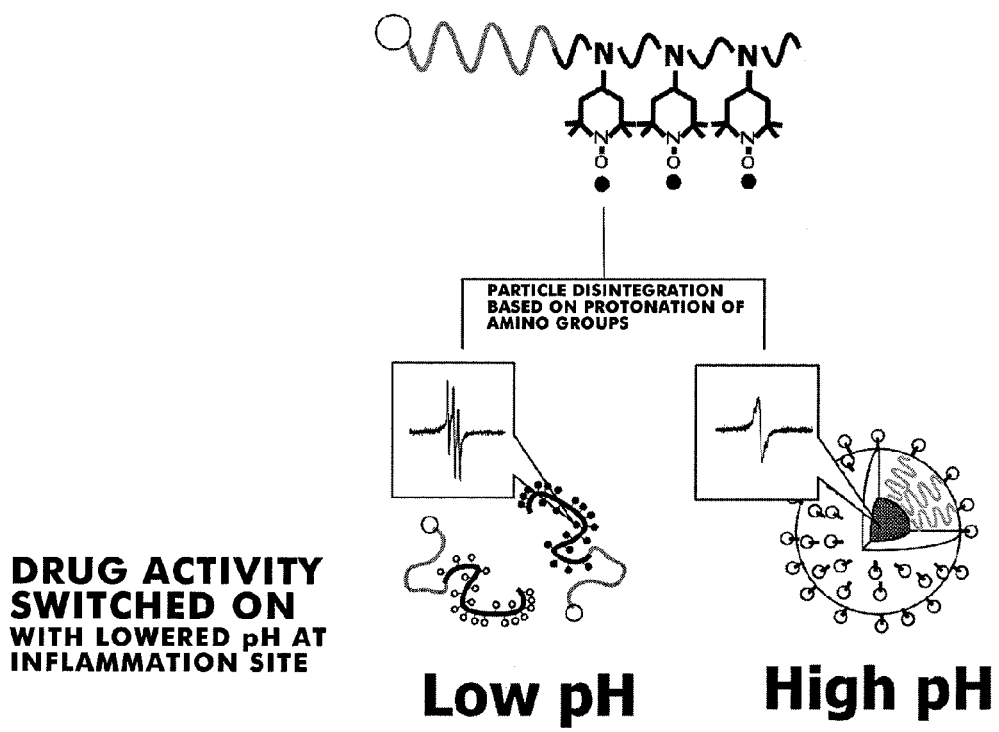
FIG. 19 is an overview explaining the pH-responsiveness of the nanoparticle (N-TEMPO-RNP) comprising the acetal-PEG-b-PCMS-N-TEMPO of the present invention.

To N-TEMPO-RNP-H (46 mM, 60 μL), an aqueous solution of $H_2O_2$ (500 mM, 60 μL) and Horseradish peroxidase (HRP)/100 mM Britton Robinson (375 U/mL, 480 μL) were added, oxidation reaction of N-TEMPO-RNP-H was performed at acidic pH (pH 5.6) and neutral pH (pH 7.4) to observe the change in ESR spectra. While the rate of oxidation reaction is known to decrease with the pH becoming acidic in general for small molecule TEMPOL, when polymerized micellized N-TEMPO-RNP-H was used, the ESR signal intensity was found to be enhanced remarkably only under the condition of pH 5.6. From this result, it is inferred that N-TEMPO-RNP-H can be used as a probe enabling visualization of ROS under acidic conditions around cancer and inflammatory tissue (FIG. 18).

INDUSTRIAL APPLICABILITY

As described above, the cyclic nitroxide radical stabilization method provided by the present invention, and the polymerized compound provided by the method, can be used in the fields of medicine and diagnostic, particularly since in vitro stabilization of a stable radical is achieved.

What is claimed is:

1. A polymerized nitroxide radical compound comprising a poly(ethylene glycol) chain segment in which the repeating unit of ethylene glycol is 15 to 10,000 and a polystyrene chain segment in which the repeating unit of styrene is 3 to 3,000, and at least 10% of the repeating units of styrene in the polystyrene chain segment at position 4 of the phenyl group, a residue of cyclic nitroxide radical compound being covalently bonded through a linking group selected from the group consisting of —CH$_2$NH—, —CH$_2$NHCH$_2$—, —CH$_2$O—, —CH$_2$OCH$_2$—, —CH$_2$OCO— and —CH$_2$OCOCH$_2$—, and when present, the remainder of the position 4 being a halogen atom, a hydrogen atom or a hydroxyl group, and the cyclic nitroxide radical compound being selected from the group consisting of 2,2,6,6-tetramethylpiperidine-1-oxyl-4-yl, 2,2,5,5-tetramethylpyrrolidine-1-oxyl-3-yl, 2,2,5,5-tetramethylpyrroline-1-oxyl-3-yl and 2,4,4-trimethyl-1,3-oxazolidine-3-oxyl-2-yl, 2,4,4-trimethyl-1,3-thiazolidine-3-oxyl-2-yl and 2,4,4-trimethyl-imidazolidine-3-oxyl-2-yl.

2. The compound according to claim 1, represented by General Formula (II)

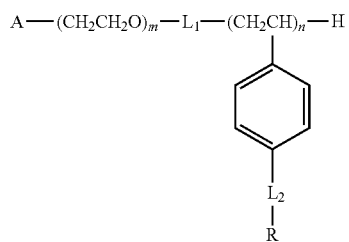

(II)

where A represents a non-substituted or substituted C$_1$-C$_{12}$ alkoxy, when substituted the substituent represents a formyl group or a group of formula R$^1$R$^2$CH—, where R$^1$ and R$^2$ are independent and represent a C$_1$-C$_4$ alkoxy or R$^1$ and R$^2$ are combined and represent —OCH$_2$CH$_2$O—, —O(CH$_2$)$_3$O— or —O(CH$_2$)$_4$O—, L$_1$ represents a linking group selected from the group consisting of a valence bond, —(CH$_2$)$_c$S—, —CO(CH$_2$)$_c$S—, where c represents an integer from 1 to 5, L$_2$ represents a linking group selected from the group consisting of methyl imino, methyl iminomethyl, methyloxy, methyloxymethyl, methyl ester and methyl ester methyl, at least 50% of n in the total number of R represents a residue of cyclic nitroxide radical compound selected from the group consisting of 2,2,6,6-tetramethylpiperidine-1-oxyl-4-yl, 2,2,5,5-tetramethylpyrrolidine-1-oxyl-3-yl, 2,2,5,5-tetramethylpyrroline-1-oxyl-3-yl and 2,4,4-trimethyl-1,3-oxazolidine-3-oxyl-2-yl, 2,4,4-trimethyl-1,3-thiazolidine-3-oxyl-2-yl and 2,4,4-trimethyl-imidazolidine-3-oxyl-2-yl, and when present the remaining R represents a hydrogen atom, a halogen atom or a hydroxy group, m represents an integer from 20 to 5,000 and
n represents an integer from 3 to 1,000.

3. The compound according to claim 2, wherein, in General Formula (II), L$_1$ is a valence bond or —CH$_2$CH$_2$S—, L$_2$ is methyl imino or methyl iminomethyl and the entirety of R comprises residues of cyclic nitroxide radical compound represented by any of the following formulae

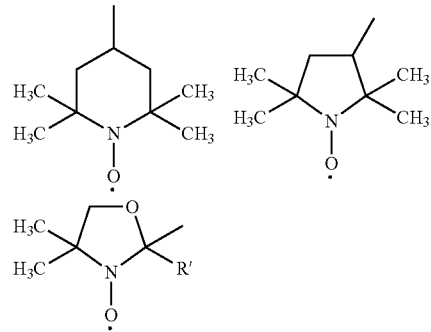

4. An antioxidant comprising the compound according to claim 1 as an active ingredient and a diluent or excipient allowed in food or pharmaceuticals.

* * * * *